US008935102B2

(12) United States Patent
Zucman-Rossi et al.

(10) Patent No.: US 8,935,102 B2
(45) Date of Patent: Jan. 13, 2015

(54) METHOD OF HEPATOCELLULAR CARCINOMA CLASSIFICATION AND PROGNOSIS

(75) Inventors: Jessica Zucman-Rossi, Paris (FR); Aurélien De Reynies, Paris (FR); David Rickman, New York, NY (US); Sandrine Boyault, Meyzieu (FR)

(73) Assignee: Institut National de la Sante et de la Recherche Medicale (Inserm), Paris (FR)

( * ) Notice: Subject to any disclaimer, the term of this patent is extended or adjusted under 35 U.S.C. 154(b) by 1765 days.

(21) Appl. No.: 12/095,604

(22) PCT Filed: Nov. 30, 2006

(86) PCT No.: PCT/EP2006/069175
§ 371 (c)(1),
(2), (4) Date: Sep. 8, 2009

(87) PCT Pub. No.: WO2007/063118
PCT Pub. Date: Jun. 7, 2007

(65) Prior Publication Data
US 2010/0015605 A1    Jan. 21, 2010

(30) Foreign Application Priority Data

Nov. 30, 2005  (EP) .................................... 05292533

(51) Int. Cl.
*G01N 31/00* (2006.01)
*C12Q 1/68* (2006.01)
*G06F 19/20* (2011.01)
*G06F 19/24* (2011.01)

(52) U.S. Cl.
CPC ........ *C12Q 1/6886* (2013.01); *C12Q 2600/106* (2013.01); *C12Q 2600/112* (2013.01); *C12Q 2600/118* (2013.01); *C12Q 2600/136* (2013.01); *C12Q 2600/154* (2013.01); *G06F 19/20* (2013.01); *G06F 19/24* (2013.01)
USPC .......................................................... 702/29

(58) Field of Classification Search
None
See application file for complete search history.

(56) References Cited

U.S. PATENT DOCUMENTS

2005/0089895 A1    4/2005 Cheung et al.

FOREIGN PATENT DOCUMENTS

WO    WO 2005/005601 A2    1/2005

OTHER PUBLICATIONS

Gygi et al., Molecular and Cellular Biology, Mar. 1999, pp. 1720-1730.*
EPO International Search Report, Feb. 2, 2007, Re: PCT/EP2006/069175, 7 pages.
Iizuka et al., "Self-organizing-map-based molecular signature representing the development of hepatocellular carcinoma", FEBS Letters, 2005, pp. 1089-1100, vol. 579, Elsevier B.V.
Okabe et al., "Genome-wide Analysis of Gene Expression in Human Hepatocellular Carcinomas Using cDNA Microarray: Identification of Genes Involved in Viral Carcinogenesis and Tumor Progression", Cancer Research, Mar. 1, 2001, pp. 2129-2137, vol. 61, American Association for Cancer Research.
Laurent-Puig et al., "Genetic Alteration Associated With Hepatocellular Carcinomas Define Distinct Pathways of Hepatocarcinogenesis", Gastronenterology, 2001, pp. 1763-1773, vol. 120, American Gastroenterological Society.
Delpuech et al., "Identification, using cDNA macroarray analysis, of distinct gene expression profiles associated with pathological and virological features of hepatocellular carcinoma", Oncogene, 2002, pp. 2926-2937, vol. 21, Nature Publishing Group.
Dudoit et al., "Comparison of Discrimination Methods for the Classification of Tumors Using Gene Expression Data", Journal of the American Statistical Association, Mar. 2002, pp. 77-87, vol. 97, No. 457, American Statistical Association.

* cited by examiner

*Primary Examiner* — Pablo S Whaley
(74) *Attorney, Agent, or Firm* — Buchanan Ingersoll & Rooney PC

(57) ABSTRACT

Methodology for the in vitro classification and/or prognosis of hepatocellular carcinoma (HCC) from a HCC sample is based on the determination of the expression profile of particular gene combinations. For example, in one embodiment, a method comprises measuring the expression level in an HCC sample of at least 8 genes selected from the group consisting of: RAB1A, REG3A, NRAS, RAMP3, MERTK, PIR, EPHA1, LAMA3, G0S2, HN1, PAK2, AFP, CYP2C9, CDH2, HAMP, SAE1, ADH6, DCN, FLJ10159, ALDH1L1, IGF1, LECT2, SLC38A1, SPARCL1, CTNNA2, GLUL, LEF1, MATN2, MME, PFN2, SPINT2, TBX3, and FGFR2; b) calculating 6 subgroup distances from the expression profile; and c) classifying the HCC tumor in the subgroup for which the subgroup distance is the lowest, wherein the 6 subgroups G1, G2, G3, G4, G5, and G6 are defined by the presence (+) or absence (−) of their clinical and genetic features.

18 Claims, 9 Drawing Sheets

Figure 1

HCC 303 G5      HCC 305 G6

METHOD OF HEPATOCELLULAR CARCINOMA CLASSIFICATION AND PROGNOSIS

CROSS-REFERENCE TO PRIORITY/PCT APPLICATIONS

This application claims priority under 35 U.S.C. §119 of EP 05292533.6, filed Nov. 30, 2005, and is the national stage of PCT/EP 2006/069175, filed Nov. 30, 2006 and designating the United States on Jun. 7, 2007, which was published as WO 2007/063118 A1, each hereby expressly incorporated by reference in its entirety and each assigned to the assignee hereof.

The present invention concerns methods for the in vitro classification and/or prognosis of hepatocellular carcinoma (HCC). The present methods are based on the determination of the expression profile of particular gene combinations.

Hepatocellular carcinoma (HCC) is one of the most frequent solid tumors worldwide and represents the third cause of mortality among deaths from cancer (Bosch. F. X., et al. Semin Liver Dis 19, 271-85 (1999)). Its frequency is particularly high in Asia and Africa due to the high frequency of viral hepatitis infections and to Aflatoxin B1 exposure (AFB1). Over the last 10 years the incidence of HCC has noticeably increased in United Kingdom, France and United States (Taylor-Robinson, S. D. et al. Bmj 319, 640 (1999); Deuffic, S. et al. Lancet 351, 214-5 (1998). El-Serag, H. B. & Mason, A. C. N Engl J Med 340, 745-50 (1999)). This increase is linked to the increase of viral hepatitis C infections.

Liver cirrhosis of any origin and dysplastic regenerative nodules have long been considered to be the likely precursors of HCC because of their frequent association with the HCC occurrence (Edmondson, H. A. & Peters, R. L. *Semin Roentgenol* 18, 75-83 (1983); Thorgeirsson, S. S. & Grisham, J. W. *Nat Genet* 31, 339-46 (2002)). As in other solid tumors, a large number of genetic alterations accumulate during the carcinogenetic process. Some of these genetic alterations are specific to HCC etiological factors, particularly HBV infection which can induce chromosome instability (Aoki, H., et al. *Proc Natl Acad Sci USA* 93, 7300-4 (1996)) or insertional mutagenesis (Brechot, C. *Gastroenterology* 127, S56-61 (2004)). The other genetic alterations specifically associated with risk factors are the R249S TP53 gene mutation in Aflatoxin B1 exposed HCCs (Bressac, B. et al. *Proc Natl Acad Sci USA* 87, 1973-7 (1990)), KRAS2 mutations observed in vinyl chloride associated HCCs (Weihrauch, M. et al. *Br J Cancer* 84, 982-9 (2001)) and TCF1 mutations associated with hepatocellular adenomas (Bluteau, O. et al. *Nat Genet* 32, 312-5 (2002)). Among the genetic alterations unrelated to HCC risk factors, microsatellite allelotypes and comparative genomic hybridization (CGH) studies have demonstrated recurrent chromosome aberrations. The most frequently deleted chromosome arms are 17p, 8p, 16q, 16p, 4q, 9p, 13q, 1p and 6q whereas the most frequent gains are found on chromosomes 1q, 7q, 8q et 17q (Boige, V. et al. *Cancer Res* 57, 1986-90 (1997); Wong, N. et al. *Clin Cancer Res* 6, 4000-9 (2000); Guan, X. Y. et al. *Genes Chromosomes Cancer* 29, 110-6 (2000)). HCC is thus a very heterogeneous group of tumors that differ by risk factors and genetic alterations.

This results in a need for a more precise, reliable and easy to perform classification of HCC tumors. Indeed, it is for instance very difficult to search for efficient therapies against very heterogeneous tumors. In contrast, a reliable classification of HCC would allow to study each subgroup separately and to find out new targeted therapies for each subgroup. A reliable and easy to perform classification test would then allow to choose for each patient an adapted treatment.

In particular, the prognosis of HCC is also very heterogeneous. Currently, the main treatment of HCC is surgical removal of HCC tumor, which may or not be followed by adjuvant chemotherapy. Chemotherapy may be very tiresome and painful for patients but is necessary in case of HCC with poor prognosis. A classification and prognosis method of HCC tumors would thus also be very helpful to decide whether or not to administer an adjuvant therapy to an HCC patient.

HCC heterogeneity is well known to those skilled in the art, and quite a lot of efforts have been made to better classify and/or prognose HCC tumors in the prior art.

For instance, several groups have recently tried to classify HCC tumors by global transcriptome analysis. Some of them describe significant expression profiles alterations between HBV and HCV derived HCC respectively (Okabe et al. Cancer Res. 2001 Mar. 1; 61(5):2129-37; Iizuka et al. Cancer Res. 2002 Jul. 15; 62(14):3939-44).

Others describe a HCC classification into two or three subgroups based on various histological features (Chung et al. Mol Cells. 2002 Dec. 31; 14 (3):382-7; Chen et al. Mol Biol Cell. 2002 June; 13(6):1929-39; WO 2004/090163) or on survival probability (Lee et al. Hepatology. 2004 September; 40(3):667-76).

The inventors, in particular, have previously shown that genetic alterations are indeed closely associated with clinical characteristics of HCC defining two groups of HCC (Legoix, P. et al. *Oncogene* 18, 4044-6 (1999); Laurent-Puig, P. et al. *Gastroenterology* 120, 1763-73 (2001)). The first type of HCC was associated with not only a high level of chromosome instability, frequent TP53 and AXIN1 mutations but also closely linked to HBV infection and a bad prognosis. Conversely, the second subgroup of HCC tumors are chromosome stable, with a high incidence of activating β-catenin alterations and not associated with viral infection.

Concerning prognosis, several groups have described genes implicated in vascular invasion (Chen et al. Mol Biol Cell. 2002 June; 13(6):1929-39; Qin et al. J Cancer Res Clin Oncol. 2004 September; 130(9):497-513) or metastasis (Qin et al. J Cancer Res Clin Oncol. 2004 September; 130(9):497-513; Ye et al. Nat Med. 2003 April; 9(4):416-23).

Others have identified groups of genes that allow for a relapse (Kurokawa et al. J Hepatol. 2004 August; 41(2):284-91; Iizuka et al. Lancet. 2003 Mar. 15; 361(9361):923-9; WO 2005/017150) and/or survival (Lee et al. Hepatology. 2004 September; 40(3):667-76; WO 2005/017150) prognosis.

However, classification of HCC tumors into two, or even three subgroups, based only on histological or genetic features, is not probable to reflect precisely HCC high heterogeneity. In addition, there is still a need for a simple, easy to perform prognosis test.

To further investigate genotype-phenotype correlations in HCC, identify pathways and/or biological processes deregulated in such heterogeneous tumors and find new prognostic factors, the inventors thus performed a comprehensive analysis at the clinical, genetic and transcriptomic level of a large series of 123 tumors.

Although most prior studies were only able to subdivide HCC tumors into two subgroups, the inventors surprisingly found that HCC tumors actually clustered into 6 distinct subgroups, closely associated with various clinical and genetic alterations. They also determined a 16-gene diagnostic predictor and a 24-gene predictor of class membership as well as a 5-gene signature predicting patient prognosis irrespective of HCC subgroup and which outperforms common clinical prognostic markers.

More precisely, the inventors have defined 6 distinct HCC subgroups or classes (hereafter named G1 to G6). These 6 subgroups were defined by a non-supervised analysis of global transcriptomic analysis of 57 HCC, 3 hepatocellular adenomas and 5 samples of pooled non-tumor tissue using Affymetrix HG-U133A GeneChip™ arrays. The 6 subgroups are highly associated with clinical and genetic factors, as displayed in the following Table 1, and summarized in FIG. 1.

TABLE 1

Associated clinical and genetic features with HCC subgroups

| | Affymetrix | QRT-PCR | |
|---|---|---|---|
| | hybridizations (57 HCC) | Validation set (63 HCC) | Complete set (109 HCC) |
| G1 | | | |
| HBV low copy number | 0.03 | 0.04 | $<10^{-5}$ |
| AFP > 100 IU/ml | 0.01 | 0.006 | $<10^{-4}$ |
| african origin | 0.005 | 0.3* | 0.004 |
| female | 0.06 | 0.05 | 0.002 |
| Axin1 mutation | 0.1 | 0.009 | 0.001 |
| 16q LOH | 0.05 | 0.04 | 0.001 |
| G2 | | | |
| HBV high copy nb | $<10^{-4}$ | 0.07 | 0.004 |
| hemochromatosis | 1* | 0.005* | 0.03 |
| portal invasion | 0.6 | 0.05 | 0.01 |
| PIK3CA mutation | 0.009* | — | — |
| G3 | | | |
| TP53 R249S mutation | 0.3* | 0.002* | 0.004 |
| CDKN2A methylation | 0.04 | 0.1 | 0.01 |
| 17p LOH | 0.02 | 0.004 | 0.0002 |
| 5q LOH | 0.02 | 0.02* | 0.004 |
| 19p LOH | 0.002 | 0.4* | 0.004 |
| 21q LOH | 0.001 | 0.05 | $<10^{-3}$ |
| 22q LOH | 0.007 | 0.02* | $<10^{-4}$ |
| G1, G2, G3 | | | |
| FAL | $<10^{-3}$ | $<10^{-3}$ | $<10^{-5}$ |
| 4q LOH | $<10^{-3}$ | 0.002 | $<10^{-5}$ |
| 16p LOH | 0.005 | 0.05 | $<10^{-3}$ |
| Early relapse | 0.005 | 1 | 0.3 |
| Early death | 0.05 | 0.7 | 0.4 |
| G1, G2 | | | |
| Age < 63 years | 0.03 | 0.08 | 0.001 |
| 13q LOH | 0.08 | 0.0001 | $<10^{-4}$ |
| 1p LOH | 0.1 | 0.02 | 0.007 |
| G2, G3 | | | |
| TP53 mutation | 0.03 | 0.001 | 0.0001 |
| G4 | | | |
| TCF1** mutation | 0.01* | —* | —* |
| no vascular invasion | 0.2 | 0.03 | 0.01 |

TABLE 1-continued

Associated clinical and genetic features with HCC subgroups

| | Affymetrix | QRT-PCR | |
|---|---|---|---|
| | hybridizations (57 HCC) | Validation set (63 HCC) | Complete set (109 HCC) |
| G6 | | | |
| Satellite nodules | 0.005 | — | 0.0005 |
| G5, G6 | | | |
| CDH1 methylation | 0.01 | 0.007 | $<10^{-3}$ |
| CTNNB1 mutation | $<10^{-10}$ | $<10^{-5}$ | $<10^{-12}$ |

Shown are P values obtained from Fisher exact tests based on the given genetic or clinical variable and (i) the original cluster groups for the Affymetrix GeneChip series (ii) the predicted cluster group (based on the 16-gene predictor) for the QRT-PCR series.
*Equal or less than 5 samples with this feature in the tested set of tumors.
**including the 3 adenoma samples As described in more details in Example 2, paragraph 2.2, the 6 subgroups may be defined using their main features as described in following Table 2.

TABLE 2

Definition of the 6 subgroups by the presence (+) or absence (−) of clinical and genetic main features.

| | G1 | G2 | G3 | G4 | G5 | G6 |
|---|---|---|---|---|---|---|
| Chromosome instability | + | + | + | − | − | − |
| Early relapse and death | + | + | + | − | − | − |
| TP53 mutation | − | + | + | − | − | − |
| HBV infection | + | + | − | − | − | − |
| Low copy number | + | − | − | − | − | − |
| High copy number | − | + | − | − | − | − |
| CTNNB1 mutation | − | − | − | − | + | + |
| Satellite nodules | − | − | − | − | − | + |

The methods of classification according to the invention allow to easily determine for any HCC liver sample to which of these 6 HCC subgroups it belongs.

The invention thus first concerns a method of in vitro classification of a HCC tumor between 6 subgroups from a liver HCC sample of a subject suffering from HCC, comprising:

a) determining an expression profile comprising or consisting of a combination of at least 8, at least 10, at least 12, at least 14, or at least 16 genes selected from the group consisting of: RAB1A, REG3A, NRAS, RAMP3, MERTK, PIR, EPHA1, LAMA3, G0S2, HN1, PAK2, AFP, CYP2C9, CDH2, HAMP, SAE1, ADH6, DCN, FLJ10159, ALDH1L1, IGF1, LECT2, SLC38A1, SPARCL1, CTNNA2, GLUL, LEF1, MATN2, MME, PFN2, SPINT2, TBX3, and FGFR2;

b) calculating from said expression profile 6 subgroup distances; and c) classifying said HCC tumor in the subgroup for which the subgroup distance is the lowest, wherein the 6 subgroups G1, G2, G3, G4, G5, and G6 are defined by their clinical and genetic features described in Table 2.

The main features of the first set of genes implicated in HCC classification are described in the following Table 3.

TABLE 3

First genes set implicated in HCC classification.

| Gene symbol* | HUGO Gene name* | "Entrez Gene" Gene ID** |
|---|---|---|
| RAB1A | RAB1A, member RAS oncogene family | 5861 |
| REG3A | regenerating islet-derived 3 alpha | 5068 |
| NRAS | neuroblastoma RAS viral (v-ras) oncogene homolog | 4893 |
| RAMP3 | receptor (calcitonin) activity modifying protein 3 | 10268 |
| MERTK | c-mer proto-oncogene tyrosine kinase | 10461 |
| PIR | pirin (iron-binding nuclear protein) | 8544 |
| EPHA1 | EPH receptor A1 | 2041 |
| LAMA3 | laminin, alpha 3 | 3909 |
| G0S2 | G0/G1switch 2 | 50486 |
| HN1 | hematological and neurological expressed 1 | 51155 |
| PAK2 | p21 (CDKN1A)-activated kinase 2 | 5062 |
| AFP | alpha-fetoprotein | 174 |
| CYP2C9 | cytochrome P450, family 2, subfamily C, polypeptide 9 | 1559 |
| CDH2 | cadherin 2, type 1, N-cadherin (neuronal) | 1000 |
| HAMP | hepcidin antimicrobial peptide | 57817 |
| SAE1 | SUMO-1 activating enzyme subunit 1 | 10055 |
| ADH6 | alcohol dehydrogenase 6 (class V) | 130 |
| DCN | decorin | 1634 |
| FLJ10159 | Hypothetical protein FLJ10159 | 55084 |
| ALDH1L1 | aldehyde dehydrogenase 1 family, member L1 | 10840 |
| IGF1 | insulin-like growth factor 1 (somatomedin C) | 3479 |
| LECT2 | leukocyte cell-derived chemotaxin 2 | 3950 |
| SLC38A1 | solute carrier family 38, member 1 | 81539 |
| SPARCL1 | SPARC-like 1 (mast9, hevin) | 8404 |
| CTNNA2 | catenin (cadherin-associated protein), alpha 2 | 1496 |
| GLUL | glutamate-ammonia ligase (glutamine synthetase) | 2752 |
| LEF1 | lymphoid enhancer-binding factor | 51176 |
| MATN2 | matrilin 2 | 4147 |
| MME | membrane metallo-endopeptidase (neutral endopeptidase, enkephalinase, CALLA, CD10) | 4311 |
| PFN2 | profilin 2 | 5217 |
| SPINT2 | serine peptidase inhibitor, Kunitz type, 2 | 10653 |
| TBX3 | T-box 3 (ulnar mammary syndrome) | 6926 |
| FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | 2263 |

*All genes symbols and names are according to the HUGO Gene Nomenclature Committee (available at http://www.gene.ucl.ac.uk/nomenclature/)
**All available information concerning the listed genes of Table 3 can be retrieved from the "Entrez Gene" portal (http://www.ncbi.nlm.nih.gov/entrez/query.fcgi?CMD=search&DB=gene) using the "Entrez Gene" Gene ID provided in Table 3.

According to the invention, a "classification" of HCC tumors is intended to mean the determination for any HCC tumor of the HCC "subgroup" or "class" (these two words "subgroup" and "class" will be used indifferently for one another throughout the application) to which it belongs, wherein the subgroups are defined by the features described in Table 2.

In a preferred embodiment of a method of in vitro classification according to the invention, the expression profile comprises or consists of at least 8, at least 10, at least 12, at least 14, or at least 16 genes selected from the group consisting of: RAB1A, REG3A, NRAS, RAMP3, MERTK, PIR, EPHA1, LAMA3, G0S2, HN1, PAK2, AFP, CYP2C9, CDH2, HAMP, SAE1, ADH6, DCN, FLJ10159, ALDH1L1, IGF1, LECT2, SLC38A1, SPARCL1.

In a more preferred embodiment of a method of in vitro classification according to the invention, the expression profile comprises or consists of at least 8, at least 10, at least 12, at least 14, or 16 genes selected from the group consisting of: RAB1A, REG3A, NRAS, RAMP3, MERTK, PIR, EPHA1, LAMA3, G0S2, HN1, PAK2, AFP, CYP2C9, CDH2, HAMP, and SAE1. In a most preferred embodiment of a method of in vitro classification according to the invention, the expression profile comprises or consists of the following 16 genes combination: RAB1A, REG3A, NRAS, RAMP3, MERTK, PIR, EPHA1, LAMA3, G0S2, HN1, PAK2, AFP, CYP2C9, CDH2, HAMP, and SAE1.

The invention also concerns another method of in vitro classification of a HCC tumor between 6 subgroups from a liver HCC sample of a subject suffering from HCC, comprising:

a) determining an expression profile comprising or consisting of a combination of at least 8, at least 10, at least 12, at least 14, at least 16, at least 18, at least 20, at least 22, or 24 genes selected from the group consisting of: ALDH1L1, CD24, CD74, CFHR3, CYP4F12, DNAJA3, DSCR1, EPHA1, EPHB4, FAAH, FGFR2, FLJ10159, GLT8D1, HAL, MATN2, MRPS7, PAK2, PLXNB1, RAB1A, RHOQ, SLC27A5, SLPI, SMARCE1, STRA13;

b) calculating from said expression profile 6 subgroup distances; and c) classifying said HCC tumor in the subgroup for which the subgroup distance is the lowest, wherein the 6 subgroups G1, G2, G3, G4, G5, and G6 are defined by their clinical and genetic features described in Table 2.

The main features of the second set of genes implicated in HCC classification are described in the following Table 4.

TABLE 4

Second genes set implicated in HCC classification

| Gene symbol* | HUGO Gene name* | "Entrez Gene" Gene ID** | Chromosomal Location | Other aliases |
|---|---|---|---|---|
| ALDH1L1 | formyltetrahydrofolate dehydrogenase | 10840 | chr3q21.2 | FTHFD |
| CD24 | CD24 antigen (small cell lung carcinoma cluster 4 antigen) | 934 | chr6q21 | CD24A |

TABLE 4-continued

Second genes set implicated in HCC classification

| Gene symbol* | HUGO Gene name* | "Entrez Gene" Gene ID** | Chromosomal Location | Other aliases |
|---|---|---|---|---|
| CD74 | CD74 antigen | 972 | chr5q32 | DHLAG, HLADG, Ia-GAMMA, protein 41 |
| CFHR3 /// CFHR4 | complement factor H related 3 /// complement factor H-related complement factor H-related 4 | 10878 /// 10877 | chr1q32 | CFHL3, DOWN16, FHR-3, FHR3, HLF4 /// CFHL4, FHR-4, FHR4, RP4-608O15.2 |
| CYP4F12 | cytochrome P450, family 4, subfamily F, polypeptide 12 | 66002 | chr19p13.1 | F22329_1 |
| DNAJA3 | DnaJ (Hsp40) homolog, subfamily A, member 3 | 9093 | chr16p13.3 | FLJ45758, TID1, hTid-1 |
| DSCR1 | Down syndrome critical region gene 1 | 1827 | chr21q22.1-q22.2| 21q22.12 | ADAPT78, CSP1, DSC1, MCIP1, RCN1 |
| EPHA1 | EphA1 | 2041 | chr7q34 | EPH, EPHT, EPHT1 |
| EPHB4 | EphB4 | 2050 | chr7q22 | HTK, MYK1, TYRO11 |
| FAAH | fatty acid amide hydrolase | 2166 | chr1p35-p34 | MGC102823, MGC138146 |
| FGFR2 | fibroblast growth factor receptor 2 | 2263 | chr10q26 | BEK, BFR-1, CD332, CEK3, CFD1, ECT1, JWS, K-SAM, KGFR, TK14, TK25 |
| FLJ10159 | hypothetical protein FLJ10159 | 55084 | chr6q21 | |
| GLT8D1 | glycosyltransferase 8 domain containing 1, or glycosyltransferase AD-017 | 55830 | chr3p21.1 | AD-017, DKFZp781O20198, FLJ14611, MSTP139 |
| HAL | histidine ammonialyase | 3034 | chr12q22-q24.1 | HIS, HSTD, histidase |
| MATN2 | matrilin 2 | 4147 | chr8q22 | |
| MRPS7 | mitochondrial ribosomal protein S7 | 51081 | chr17q25 | MRP-S, MRP-S7, RP-S7, RPMS7 |
| PAK2 | p21 (CDKN1A)-activated kinase 2 | 5062 | chr3q29 | PAK65, PAKgamma |
| PLXNB1 | plexin B1 | 5364 | chr3p21.31 | KIAA0407, PLEXIN-B1, PLXN5, SEP |
| RAB1A | RAB1A, member RAS oncogene family | 5861 | chr2p14 | DKFZP564B163, RAB1 |
| RHOQ | ras homolog gene family, member Q | 23433 | chr2p21 | ARHQ, RASL7A, TC10, TC10A |
| SLC27A5 | solute carrier family 27 (fatty acid transporter), member 5 | 10998 | chr19q13.43 | ACSB, ACSVL6, FACVL3, FATP5, FLJ22987, VLACSR, VLCSH2, VLCSH2 |
| SLPI | secretory leukocyte protease inhibitor (antileukoproteinase) | 6590 | chr20q12 | ALK1, ALP, BLPI, HUSI, HUSI-I, MPI, WAP4, WFDC4 |
| SMARCE1 | SWI/SNF related, matrix associated, actin dependent regulator of chromatin, subfamily e, member 1 | 6605 | chr17q21.2 | BAF57 |
| STRA13 | stimulated by retinoic acid 13 | 201254 | ch17q25.3 | E3, MGC14480 |

*All genes symbols and names are according to the HUGO Gene Nomenclature Committee (available at http://www.gene.ucl.ac.uk/nomenclature/)
**All available information concerning the listed genes of Table 4 can be retrieved from the "Entrez Gene" portal (http://www.ncbi.nlm.nih.gov/entrez/query.fcgi?CMD=search&DB=gene) using the "Entrez Gene" Gene ID provided in Table 4.

In a preferred embodiment of the above method of in vitro classification according to the invention using the second set of genes, the expression profile comprises or consists of the following 24 genes combination: ALDH1L1, CD24, CD74, CFHR3, CYP4F12, DNAJA3, DSCR1, EPHA1, EPHB4, FAAH, FGFR2, FLJ10159, GLT8D1, HAL, MATN2, MRPS7, PAK2, PLXNB1, RAB1A, RHOQ, SLC27A5, SLPI, SMARCE1, STRA13.

According to the invention, a "liver HCC sample" is intended to mean any liver sample comprising HCC tumor tissue. In a preferred embodiment of a method of in vitro classification according to the invention, the liver HCC sample is a liver HCC biopsy or a HCC tumor surgical resection.

By "determining an expression profile" is meant the measure of the expression level of a group a selected genes. The expression level of each gene may be determined in vitro either at the proteic or at the nucleic level, using any technology known in the art.

For instance, at the proteic level, the in vitro measure of the expression level of a particular protein may be performed by any dosage method known by a person skilled in the art, including but not limited to ELISA or mass spectrometry analysis. These technologies are easily adapted to any HCC sample. Indeed, proteins of the HCC sample may be extracted using various technologies well known to those skilled in the art for ELISA or mass spectrometry in solution measure. Alternatively, the expression level of a protein in a HCC tumor slice may be analysed using mass spectrometry directly on the tissue slice.

In a preferred embodiment of a method of in vitro classification according to the invention, the expression profile is determined in vitro at the nucleic level. At the nucleic level, the in vitro measure of the expression level of a gene may be carried out either directly on messenger RNA (mRNA), or on retrotranscribed complementary DNA (cDNA). Any method to measure the expression level may be used, including but not limited to microarray analysis, quantitative PCR, southern analysis. In a preferred embodiment of a method of in vitro classification according to the invention the expression profile is determined in vitro using a microarray. In another preferred embodiment of a method of in vitro classification according to the invention, the expression profile is determined in vitro using quantitative PCR. In any case, the expression level of any gene is preferably normalized in comparison to the expression level of an internal control gene, generally a household gene, including but not limited to ribosomal RNA (such as for instance 18S ribosomal RNA) or genes such as actin or HPRT. These technologies are also easily adapted to any HCC sample. Indeed, several well known technologies are available to those skilled in the art for extracting mRNA from a tissue sample and retrotranscribing mRNA into cDNA.

In a preferred embodiment, when using a method of in vitro classification involving the first set of genes (see Table 3), the expression profile is determined in vitro at the nucleic level using quantitative PCR. In another preferred embodiment, when using a method of classification involving the second set of genes (see Table 4), the expression profile is determined in vitro at the nucleic level using a nucleic acid microarray. In particular, Affimetrix microarray U133A may be advantageously used.

In any method of in vitro classification of a HCC tumor between the 6 subgroups defined by the inventors, for each subgroup, a "subgroup distance" is calculated, which represents a mathematical distance between said HCC tumor and each of the 6 subgroups. The lowest the distance between a sample and a subgroup, the highest is the probability that said sample belongs to this particular subgroup.

For a selected combination of n genes (n≥8), the set of all tumors can be defined as a n-dimensions set in which each tumor sample may be characterized by n coordinates corresponding to the expression levels of each selected gene in said tumor sample. Each subgroup or class is a subset of the n-dimensions set that can be defined by a center point and an acceptable variation percentage around each coordinate of the center point. Depending on the technology used for the determination of the expression profile, appropriate mathematical functions permitting each to calculate the distance of any tumor sample to one of the 6 subgroups or classes may be chosen.

In particular, when the expression profile is determined using quantitative PCR, for a given HCC tumor $sample_i$ and a particular subgroup or $class_k$, the distance of said $sample_i$ to said $class_k$ may be calculated using the following formula (I):

$$\text{Distance }(sample_i, class_k) = \sum_{t=1\ldots n} \frac{(\Delta Ct(sample_i, gene_t) - \mu(class_k, gene_t))^2}{\sigma(gene_t)}, \quad (I)$$

wherein n represents the number of genes in the expression profile, for each $gene_t$, $\mu(class_k, gene_t)$ and $\sigma(gene_t)$ are parameters that depend on the chosen combination of genes and may be calculated by optimization on a training group of HCC tumors, followed by validation on a test group of HCC tumors, as described in more details in Example 2 of the present application.

Alternatively, when the expression profile is determined at the nucleic level using a nucleic acid microarray, for a given HCC tumor $sample_i$ and a particular subgroup or $class_k$, the distance of said $sample_i$ to said $class_k$, may be calculated using various formulas derived from various algorithms well known to those skilled in the art. For instance, said instance of said $sample_i$ to said $class_k$, may be calculated using the following formula (II):

$$\text{Distance }(sample_i, class_k) = \left( \frac{\sum_{t=1\ldots n}(c(gene_t, class_k))^2}{2} + 1.791759 \right) - \left( \sum_{t=1\ldots n} \frac{(y(sample_i, gene_t) - \mu(gene_t))}{\sigma(gene_t)} \times c(gene_t, class_k) \right), \quad (II)$$

wherein n represents the number of genes in the expression profile, for each $gene_t$, $y(sample_i, gene_t)$ represents the normalized intensity value for $gene_t$ in $sample_i$, and for each $gene_t$ and $class_k$, $c(gene_t, class_k)$, $\mu(gene_t)$ and $\sigma(gene_t)$ are parameters that depend on the chosen combination of genes and may be calculated by optimization on a training group of HCC tumors, followed by validation on a test group of HCC tumors, as described in more details in Example 2 of the present application.

The normalization may be performed using any well known method, for instance using RMA normalization.

For a given sample$_i$, once all distances to all classes have been calculated, the sample$_i$ predicted class is calculated according to the following formula (III):

$$\text{Predicted class }(sample_i) = \underset{k=1\ldots 6}{\arg\min}(\text{Distance}(sample_i, class_k)), \quad (III)$$

which means that the predicted class of a given sample$_i$ is the class for which the distance of sample$_i$ to the class is the lowest.

In a preferred embodiment of a method of classification of a HCC tumor between the 6 subgroups defined by the inventors using the first set of genes (see Table 3), the expression profile consists of the following genes combination: RAB1A, REG3A, NRAS, RAMP3, MERTK, PIR, EPHA1, LAMA3, G0S2, HN1, PAK2, AFP, CYP2C9, CDH2, HAMP, and SAE1, and is determined using quantitative PCR, wherein each distance of a sample$_i$ to a class$_k$ is calculated using the following formula (IV):

$$\text{Distance }(sample_i, class_k) = \sum_{t=1\ldots 16} \frac{(\Delta Ct(sample_i, gene_t) - \mu(class_k, gene_t))^2}{\sigma(gene_t)}, \quad (IV)$$

wherein for each gene$_t$ and class$_k$, the $\mu$(class$_k$, gene$_t$) and $\sigma$(gene$_t$) values are in an interval of 10%, preferably 9%, 8%, 7%, 6%, 5%; or even 4%, 3%, 2% or 1% around those displayed in the following Table 5.

In a preferred embodiment of a method of classification of a HCC tumor between the 6 subgroups defined by the inventors using the second set of genes (see Table 4), the expression profile consists of the following genes combination: ALDH1L1, CD24, CD74, CFHR3, CYP4F12, DNAJA3, DSCR1, EPHA1, EPHB4, FAAH, FGFR2, FLJ10159, GLT8D1, HAL, MATN2, MRPS7, PAK2, PLXNB1, RAB1A, RHOQ, SLC27A5, SLPI, SMARCE1, STRA13, and is determined at the nucleic level using quantitative a microarray, wherein each distance of a sample$_i$ to a class$_k$ is calculated using the following formula (V):

$$\text{Distance }(sample_i, class_k) = \quad (V)$$

$$\left( \frac{\sum_{t=1\ldots 24} (c(gene_t, class_k))^2}{2} + 1.791759 \right) -$$

$$\left( \sum_{t=1\ldots 24} \frac{(y(sample_i, gene_t) - \mu(gene_t))}{\sigma(gene_t)} \times c(gene_t, class_k) \right),$$

wherein for each gene$_t$ and class$_k$, c(gene$_t$, class$_k$), $\mu$(gene$_t$) and $\sigma$(gene$_t$) values are in an interval of 10%, preferably 9%, 8%, 7%, 6%, 5%; or even 4%, 3%, 2% or 1% around those displayed in the following Table 6.

TABLE 5

Parameters for each gene and for each class used in the above quantitative PCR Distance formula (IV)

| μ | class 1 | class 2 | class 3 | class 4 | class 5 | class 6 | σ |
|---|---------|---------|---------|---------|---------|---------|---|
| gene 1 (RAB1A) | −16.39 | −16.04 | −16.29 | −17.15 | −17.33 | −16.95 | 0.23 |
| gene 2 (PAP) | −28.75 | −27.02 | −23.48 | −27.87 | −19.23 | −11.33 | 16.63 |
| gene 3 (NRAS) | −16.92 | −17.41 | −16.25 | −17.31 | −16.96 | −17.26 | 0.27 |
| gene 4 (RAMP3) | −23.54 | −23.12 | −25.34 | −22.36 | −23.09 | −23.06 | 1.23 |
| gene 5 (MERTK) | −18.72 | −18.43 | −21.24 | −18.29 | −17.03 | −16.16 | 7.23 |
| gene 6 (PIR) | −18.44 | −19.81 | −16.73 | −18.28 | −17.09 | −17.25 | 0.48 |
| gene 7 (EPHA1) | −16.68 | −16.51 | −19.89 | −17.04 | −18.70 | −21.98 | 1.57 |
| gene 8 (LAMA3) | −20.58 | −20.44 | −20.19 | −21.99 | −18.77 | −16.85 | 2.55 |
| gene 9 (G0S2) | −14.82 | −17.45 | −18.18 | −14.78 | −17.99 | −16.06 | 3.88 |
| gene 10 (HN1) | −16.92 | −17.16 | −15.91 | −17.88 | −17.72 | −17.93 | 0.54 |
| gene 11 (PAK2) | −17.86 | −16.56 | −16.99 | −18.14 | −17.92 | −17.97 | 0.58 |
| gene 12 (AFP) | −16.68 | −12.36 | −26.80 | −27.28 | −25.97 | −23.47 | 14.80 |
| gene 13 (CYP2C9) | −18.27 | −16.99 | −16.26 | −16.23 | −13.27 | −14.44 | 5.47 |
| gene 14 (CDH2) | −15.20 | −14.76 | −18.91 | −15.60 | −15.48 | −17.32 | 10.59 |
| gene 15 (HAMP) | −19.53 | −20.19 | −21.32 | −18.51 | −25.06 | −26.10 | 13.08 |
| gene 16 (SAE1) | −17.37 | −17.10 | −16.79 | −18.22 | −17.72 | −18.16 | 0.31 |

TABLE 6

Parameters for each gene and for each class used in the above microarray Distance formula (V)

| Gene N° | Gene symbol | class 1 | class 2 | class 3 | class 4 | class 5 | class 6 | μ | σ |
|---|---|---|---|---|---|---|---|---|---|
| 1 | MATN2 | 0.70615962 | 0.194820133 | 0 | 0.251226887 | −0.43679693 | −0.95672006 | 6.86694444 | 1.3591753 |
| 2 | EPHB4 | 0.772905372 | 0 | −0.23845281 | 0 | 0 | −0.11554095 | 8.12722222 | 0.90851011 |
| 3 | SLPI | 0.348202773 | 1.150217317 | −0.30674955 | 0.772922695 | −0.92749405 | −1.03709919 | 9.19555556 | 1.58143433 |
| 4 | FAAH | 0 | −0.05721942 | −0.14546431 | 0.461062372 | 0 | 0 | 7.35527778 | 0.90656803 |
| 5 | ALDH1L1 | −0.90005519 | −0.88021827 | 0 | 0.001883282 | 0.766706969 | 0.727033118 | 9.55166667 | 1.51233112 |
| 6 | DNAJA3 | −0.38971634 | 0 | 0 | 0 | 0.115122957 | 0 | 9.20444444 | 0.79106866 |
| 7 | EPHA1 | 0.084999966 | 1.076607341 | −0.39390753 | 0.336075517 | −0.15411627 | −0.94965903 | 8.34 | 1.18158325 |
| 8 | CYP4F12 | 0 | 0 | −0.50724032 | 0 | 0.411786437 | 0 | 8.61416667 | 0.89048235 |
| 9 | CFHR4 /// CFHR3 | −0.3047186 | 0 | −0.85911235 | 0.594911312 | 0.240167858 | 0 | 9.63111111 | 1.9450676 |
| 10 | FGFR2 | 1.107271104 | 1.414413219 | 0 | −0.33319985 | −0.93870859 | −0.78623447 | 6.45694444 | 1.51938352 |
| 11 | CD24 | 0.877735471 | 0.272141138 | 0.391097168 | −0.19493988 | −0.09580985 | −1.25022405 | 6.88527778 | 1.84942286 |
| 12 | RAB1A | 0 | 0.181176347 | 0.101889323 | 0 | −0.13052075 | 0 | 10.9441667 | 0.75674426 |
| 13 | PAK2 | 0.333384856 | 0 | 0.506491717 | −0.14545539 | −0.07557739 | −0.39796907 | 7.58722222 | 1.04944811 |
| 14 | STRA13 | −0.61853503 | −0.18082898 | 0.428679271 | −0.14603227 | 0.113677426 | 0.403039586 | 9.56055556 | 0.91004758 |
| 15 | CD74 | −0.20143371 | 0 | 0 | 0 | −0.40543025 | 0.741093354 | 10.9897222 | 1.28270148 |
| 16 | SMARCE1 | 0.126430939 | 0 | 0.308479215 | −0.17753221 | 0 | −0.25610041 | 8.43638889 | 0.86973267 |
| 17 | RHOQ | 0 | 0.321593401 | 0.234570984 | 0 | −0.196463 | −0.09749623 | 8.02888889 | 0.97675881 |
| 18 | DSCR1 | −0.04133466 | −0.10070514 | −0.07191945 | 0.033538532 | 0 | 0.436538207 | 7.40194444 | 0.92638619 |
| 19 | PLXNB1 | 0.550893643 | 0.055723559 | −0.24782026 | −0.15487024 | 0 | −0.08389023 | 8.10722222 | 0.98619313 |
| 20 | HAL | 0.428036608 | 1.655082264 | −0.24462171 | 0.139158147 | −0.85676893 | −1.12088638 | 7.73055556 | 1.21158219 |
| 21 | MRPS7 | −0.24232641 | 0 | 0.552067125 | 0 | 0 | 0 | 8.77777778 | 0.88623422 |
| 22 | GLT8D1 | −0.08380816 | −0.21624193 | −0.11283474 | 0 | 0.458734818 | 0.34625682 | 9.20027778 | 0.91869819 |
| 23 | FLJ10159 | 1.275819214 | 0.257162026 | 0 | −0.03229518 | −0.27448613 | −0.99690117 | 7.33638889 | 1.60341806 |
| 24 | SLC27A5 | −0.93094948 | −0.2491716 | −0.50142942 | 0.607483755 | 0.535897078 | 0.538169671 | 9.89388889 | 1.46675337 |

The invention also concerns a method of in vitro prognosis of global survival and/or survival without relapse from a liver HCC sample of a subject suffering from HCC, comprising:

a) determining an expression profile comprising a combination of at least 2, at least 3, at least 4, or at least 5 genes selected from the group consisting of NRCAM, PIR, RAMP3, SLC21A2, TAF9, TNA, HN1, PSMD1, MRPS7, CDC20, ENO1, HLF, STRA13, RAGD, NRAS, ARFGEF2, RAB1A, G0S2, SMAD3, DNAJA3, HELO1, RHOQ, C14orf156, NPEPPS, PDCD2, PHB, KIAA0090, IMP-3, KPNA2, KIAA0268, UNQ6077, LOC440751, G6PD, STK6, TFRC, GLA, TRIP13, SPP1, AKR1C1, AKR1C2, GIMAP5, ADM, CCNB1, TKT, AGPS, RAN, NUDT9, HRASLS3, HLA-DQA1, NEU1, RARRES2, PAPOLA, ABCB6, BIRC5, FLJ20273, C14orf109, CHKA, TUBB2, HMGB3, TXNRD1, IFITM1, KIAA0992, MPPE1, KLRB1, CCL5, SYNE1, DNASE1L3, CYP2C18, PACSIN2, PON3, and PPP2R1B;

b) calculating from said expression profile a global survival score and/or a survival without relapse score; and c) comparing the obtained global survival score and/or survival without relapse score each with a threshold value, wherein
a global survival/survival without relapse score strictly inferior to said threshold value indicates a good survival/survival without relapse prognosis, whereas
a global survival/survival without relapse score superior or equal to said threshold value indicates a bad survival/survival without relapse prognosis.

The main features of the genes implicated in HCC prognosis are described in the following Table 7.

TABLE 7

Genes implicated in HCC prognosis

| Gene symbol* | HUGO Gene name* | "Entrez Gene" Gene ID** |
|---|---|---|
| NRCAM | neuronal cell adhesion molecule | 4897 |
| PIR | pirin (iron-binding nuclear protein) | 8544 |
| RAMP3 | receptor (calcitonin) activity modifying protein 3 | 10268 |
| SLCO2A1 | solute carrier organic anion transporter family, member 2A1 | 6578 |
| TAF9 | TAF9 RNA polymerase II, TATA box binding protein (TBP)-associated factor, 32 kDa | 6880 |
| CLEC3B | C-type lectin domain family 3, member B | 7123 |
| HN1 | hematological and neurological expressed 1 | 51155 |
| PSMD1 | proteasome (prosome, macropain) 26S subunit, non-ATPase, 1 | 5707 |
| MRPS7 | mitochondrial ribosomal protein S7 | 51081 |
| CDC20 | CDC20 cell division cycle 20 homolog (S. cerevisiae) | 991 |
| ENO1 | enolase 1, (alpha) | 2023 |
| HLF | hepatic leukemia factor | 3131 |

TABLE 7-continued

Genes implicated in HCC prognosis

| Gene symbol* | HUGO Gene name* | "Entrez Gene" Gene ID** |
|---|---|---|
| STRA13 | stimulated by retinoic acid 13 homolog (mouse) | 201254 |
| RRAGD | Ras-related GTP binding D | 58528 |
| NRAS | neuroblastoma RAS viral (v-ras) oncogene homolog | 4893 |
| ARFGEF2 | ADP-ribosylation factor guanine nucleotide-exchange factor 2 (brefeldin A-inhibited) | 10564 |
| RAB1A | RAB1A, member RAS oncogene family | 5861 |
| G0S2 | G0/G1switch 2 | 50486 |
| SMAD3 | SMAD, mothers against DPP homolog 3 (*Drosophila*) | 4088 |
| DNAJA3 | DnaJ (Hsp40) homolog, subfamily A, member 3 | 9093 |
| ELOVL5 | ELOVL family member 5, elongation of long chain fatty acids (FEN1/Elo2, SUR4/Elo3-like, yeast) | 60481 |
| RHOQ | ras homolog gene family, member Q | 23433 |
| C14orf156 | chromosome 14 open reading frame 156 | 81892 |
| NPEPPS | aminopeptidase puromycin sensitive | 9520 |
| PDCD2 | programmed cell death 2 | 5134 |
| PHB | prohibitin | 5245 |
| KIAA0090 | KIAA0090 | 23065 |
| IMP-3 | IGF-II mRNA-binding protein 3 | 10643 |
| KPNA2 | karyopherin alpha 2 (RAG cohort 1, importin alpha 1) | 3838 |
| KIAA0268 | C219-reactive peptide | 348477 |
| UNQ6077 | AAAP6077 | 375056 |
| LOC440751 | similar to C219-reactive peptide | 440751 |
| G6PD | glucose-6-phosphate dehydrogenase | 2539 |
| STK6 | serine/threonine kinase 6 | 6790 |
| TFRC | transferrin receptor (p90, CD71) | 7037 |
| GLA | galactosidase, alpha | 2717 |
| TRIP13 | thyroid hormone receptor interactor 13 | 9319 |
| SPP1 | secreted phosphoprotein 1 (osteopontin, bone sialoprotein I, early T-lymphocyte activation 1) | 6696 |
| AKR1C1 | aldo-keto reductase family 1, member C1 (dihydrodiol dehydrogenase 1; 20-alpha (3-alpha)-hydroxysteroid dehydrogenase) | 1645 |
| AKR1C2 | aldo-keto reductase family 1, member C2 (dihydrodiol dehydrogenase 2; bile acid binding protein; 3-alpha hydroxysteroid dehydrogenase, type III) | 1646 |
| GIMAP5 | GTPase, IMAP family member 5 | 55340 |
| ADM | adrenomedullin | 133 |
| CCNB1 | cyclin B1 | 891 |
| TKT | transketolase (Wernicke-Korsakoff syndrome) | 7086 |
| AGPS | alkylglycerone phosphate synthase | 8540 |
| RAN | RAN, member RAS oncogene family | 5901 |
| NUDT9 | nudix (nucleoside diphosphate linked moiety X)-type motif 9 | 53343 |
| HRASLS3 | HRAS-like suppressor 3 | 11145 |
| HLA-DQA1 | major histocompatibility complex, class II, DQ alpha 1 | 3117 |
| NEU1 | sialidase 1 (lysosomal sialidase) | 4758 |
| RARRES2 | retinoic acid receptor responder (tazarotene induced) 2 | 5919 |
| PAPOLA | poly(A) polymerase alpha | 10914 |
| ABCB6 | ATP-binding cassette, sub-family B (MDR/TAP), member 6 | 10058 |
| BIRC5 | baculoviral IAP repeat-containing 5 (survivin) | 332 |
| FLJ20273 | RNA-binding protein | 54502 |
| C14orf109 | chromosome 14 open reading frame 109 | 26175 |
| CHKA | choline kinase alpha | 1119 |
| TUBB2 | tubulin, beta 2 | 7280 |
| HMGB3 | high-mobility group box 3 | 3149 |
| TXNRD1 | thioredoxin reductase 1 | 7296 |
| IFITM1 | interferon induced transmembrane protein 1 (9-27) | 8519 |
| KIAA0992 | palladin | 23022 |
| MPPE1 | Metallophosphoesterase 1 | 65258 |

TABLE 7-continued

Genes implicated in HCC prognosis

| Gene symbol* | HUGO Gene name* | "Entrez Gene" Gene ID** |
|---|---|---|
| KLRB1 | killer cell lectin-like receptor subfamily B, member 1 | 3820 |
| CCL5 | chemokine (C-C motif) ligand 5 | 6352 |
| SYNE1 | spectrin repeat containing, nuclear envelope 1 | 23345 |
| DNASE1L3 | deoxyribonuclease I-like 3 | 1776 |
| CYP2C18 | cytochrome P450, family 2, subfamily C, polypeptide 18 | 1562 |
| PACSIN2 | protein kinase C and casein kinase substrate in neurons 2 | 11252 |
| PON3 | paraoxonase 3 | 5446 |
| PPP2R1B | protein phosphatase 2 (formerly 2A), regulatory subunit A (PR 65), beta isoform | 5519 |

*All genes symbols and names are according to the HUGO Gene Nomenclature Committee
**All available information concerning the listed genes of Table 7 can be retrieved from the "Entrez Gene" portal using the "Entrez Gene" Gene ID provided in Table 3.

In a preferred embodiment of a method of in vitro prognosis according to the invention, the expression profile comprises and preferably consists of a combination of at least 2, at least 3, at least 4, or at least 5 genes selected from the group consisting of NRCAM, PIR, RAMP3, SLC21A2, TAF9, TNA, HN1, PSMD1, MRPS7, CDC20, ENO1, HLF, STRA13, RAGD, NRAS, ARFGEF2, RAB1A, G0S2, SMAD3, DNAJA3, HELO1, and RHOQ.

According to the invention, a "prognosis" of HCC evolution means a prediction of the future evolution of a particular HCC tumor relative to the patient suffering of this particular HCC tumor. The methods according to the invention allow for both a global survival prognosis and a survival without relapse prognosis.

By "global survival prognosis" is meant prognosis of survival, with or without relapse. As stated before, the main current treatment against HCC is tumor surgical resection. As a result, a "bad global survival prognosis" is defined as the occurrence of death within the 3 years after liver resection, whereas a "good global survival prognosis" is defined as the lack of death during the 5 post-operative years.

By "survival without relapse prognosis" is meant prognosis of survival in the absence of any relapse. A "bad survival without relapse prognosis" is defined as the presence of tumor-relapse within the two years after liver resection, whereas a "good survival without relapse prognosis" is defined as the lack of relapse during the 4 post-operative years.

In a preferred embodiment of a method of in vitro prognosis of global survival according to the invention, the expression profile comprises and preferably consists of a genes combination selected from:
TAF9, PIR, NRCAM, and RAMP3,
TAF9, NRCAM, SLC21A2, and PSMD1,
TAF9, NRCAM, RAMP3, and PSMD1,
TAF9, NRCAM, NRAS, RAMP3, and PSMD1, or
TAF9, NRCAM, RAMP3, PSMD1 and ARFGEF2.

In a still more preferred embodiment of a method of in vitro prognosis of global survival according to the invention, the expression profile comprises and preferably consists of the following genes combination:
TAF9, NRCAM, RAMP3, PSMD1 and ARFGEF2.

Alternatively, in a preferred embodiment of a method of in vitro prognosis of survival without relapse according to the invention, the expression profile comprises and preferably consists of a genes combination selected from:
TAF9, and G0S2,
TAF9, NRCAM, and RAMP3,
TAF9, G0S2, and RAMP3,
TAF9, NRCAM, DNAJA3, and RAMP3, or
TAF9, NRCAM, G0S2, DNAJA3, and RAMP3.

In a still more preferred embodiment of a method of in vitro prognosis of survival without relapse according to the invention, the expression profile comprises and preferably consists of the following genes combination:
TAF9, NRCAM, and RAMP3.

A particular combination of genes may be referred to as a predictor.

For a method of in vitro prognosis of global survival and/or survival without relapse according to the invention, the "liver HCC sample" may also be any liver sample comprising HCC tumor tissue. In a preferred embodiment of a method of in vitro prognosis of global survival and/or survival without relapse according to the invention, the liver HCC sample is a liver HCC biopsy or a HCC tumor surgical resection.

As for methods of in vitro classification, in a method of in vitro prognosis of global survival and/or survival without relapse, the expression level of each gene may be determined in vitro either at the proteic or at the nucleic level, using any technology known in the art, in particular any technology described above.

In a preferred embodiment of a method of in vitro prognosis of global survival and/or survival without relapse, the expression profile is determined in vitro at the nucleic level. Preferably, the expression profile is determined using a microarray. In another preferred embodiment, the expression profile is determined using quantitative PCR. In any case, the expression level of any gene is preferably normalized in comparison to the expression level of an internal control gene, generally a household gene, including but not limited to ribosomal RNA (such as for instance 18S ribosomal RNA) or genes such as actin or HPRT.

In any method of in vitro prognosis of global survival and/or survival without relapse according to the invention, a global survival and/or survival without relapse "score" is calculated. For a selected combination of n genes (n≥2), a "score" is a logistic function taking into account the n expression levels of each selected gene in said tumor sample, weighted by parameters that depend on the chosen combination of genes and may be calculated by optimization on a training group of HCC tumors, followed by validation on a test group of HCC tumors, as explained in more details in Example 3 of the present application.

Depending on the technology used for the determination of the expression profile, an appropriate score function with suitable parameters may be determined.

In particular, when the expression profile is determined using quantitative PCR, for a given $sample_i$, a global survival or a survival without relapse "score" may be calculated using the following formula:

$$\text{Score}(sample_i) = \sum_{t=1 \ldots n} \beta(gene_t) \cdot (2^{-\Delta Ct(sample_i, gene_t)} - \mu(gene_t)),$$

wherein n represents the number of genes in the expression profile, for each $gene_t$, $\beta(gene_t)$ and $\mu(gene_t)$ are parameters that depend on the chosen combination of genes and may be calculated by optimization on a training group of HCC tumors, followed by validation on a test group of HCC tumors, as described in more details in Example 3 of the present application.

In any method of in vitro prognosis of global survival and/or survival without relapse according to the invention, the obtained score(s) of global survival and/or survival without relapse are then compared to at least one threshold value, which determines whether the prognosis is bad or good.

For a given combination of genes in the expression profile, such a threshold value may be determined using the same method as for $\beta(gene_t)$ and $\mu(gene_t)$ parameters, i.e. by optimization on a training group of HCC tumors, followed by validation on a test group of HCC tumors, as described in more details in Example 3 of the present application.

For a given threshold value, the prognosis of a sample will be:

a bad prognosis: if its score is superior or equal to said threshold value, or a good prognosis: if its score is strictly inferior to said threshold value.

In a preferred embodiment of a method of in vitro prognosis of global survival according to the invention, the expression profile consists of the genes combination of the following Table 8 and is determined using quantitative PCR and the following formula:

Global survival score $(sample_i) =$ $$\sum_{t=1 \ldots n} \beta(gene_t) \cdot (2^{-\Delta Ct(sample_i, gene_t)} - \mu(gene_t)),$$

wherein n represents the number of genes in the combination, t represents the number of each gene in the combination displayed in the following Table 8, and the value of each $\beta(gene_t)$ and $\mu(gene_t)$ coefficients is in an interval of 10%, preferably 9%, 8%, 7%, 6%, 5%; or even 4%, 3%, 2% or 1% around those displayed in Table 8.

TABLE 8

Preferred combination of genes (predictor) and parameters for global survival score determination.
Predictor 1

| Gene number | Gene symbol | μ | β | Threshold value |
|---|---|---|---|---|
| 1 | TAF9 | 7.28 | 0.129 | −0.393 |
| 2 | NRCAM | 1.59 | 0.252 | |
| 3 | RAMP3 | 0.14 | −6.133 | |
| 4 | PSMD1 | 4.66 | 0.024 | |
| 5 | ARFGEF2 | 3.66 | −0.025 | |

In a most preferred embodiment, the threshold value used for the global survival prognosis is in an interval of 10%, preferably 9%, 8%, 7%, 6%, 5%; or even 4%, 3%, 2% or 1% around that displayed in Table 8.

In a preferred embodiment of a method of in vitro prognosis of survival without relapse according to the invention, the expression profile consists of the genes combination of the following Table 9 and is determined using quantitative PCR and the following formula:

Survival without relapse score $(sample_i) =$ $$\sum_{t=1 \ldots n} \beta(gene_t) \cdot (2^{-\Delta Ct(sample_i, gene_t)} - \mu(gene_t))$$

wherein n represents the number of genes in the combination, t represents the number of each gene in the combination displayed in the following Table 9, and the value of each $\beta(gene_t)$ and $\mu(gene_t)$ coefficients is in an interval of 10%, preferably 9%, 8%, 7%, 6%, 5%; or even 4%, 3%, 2% or 1% around those displayed in Table 9.

TABLE 9

Preferred combination of genes (predictor) and parameters for survival without relapse score determination.
Predictor 1

| Gene number | Gene symbol | μ | β | Threshold value |
|---|---|---|---|---|
| 1 | TAF9 | 7.28 | 0.127 | −0.461 |
| 2 | NRCAM | 1.59 | 0.196 | |
| 3 | RAMP3 | 0.14 | −3.886 | |

In a most preferred embodiment, the threshold value used for the prognosis is in an interval of 10%, preferably 9%, 8%, 7%, 6%, 5%; or even 4%, 3%, 2% or 1% around that displayed in Table 9.

Preferably, $\Delta Ct(sample_i, gene_t)$ values are calculated relative to ribosomal 18S RNA (R18S).

The invention further concerns a method for the in vitro diagnosis determination of the advisability of adjuvant therapy from a liver HCC sample of a subject suffering from HCC, comprising:

a) determining a survival and/or survival without relapse prognosis according to any method according to the invention, and b) determining the advisability of adjuvant therapy from said prognosis, wherein:

in the presence of a bad prognosis, adjuvant therapy is recommended, whereas in the absence of a bad prognosis, adjuvant therapy is not recommended.

By "adjuvant therapy" is meant an additional antitumoral therapy that may be administered to a subject suffering from HCC after surgical HCC tumor resection. Adjuvant therapies may include, without being limited to, chemotherapy and radiotherapy.

The present invention also concerns a kit for the in vitro classification of a HCC tumor between 6 subgroups from a liver HCC sample of a subject suffering from HCC, comprising reagents for the in vitro determination of an expression profile comprising or consisting of a combination of at least 8, at least 10, at least 12, at least 14, or at least 16 genes selected from the group consisting of: RAB1A, REG3A, NRAS, RAMP3, MERTK, PIR, EPHA1, LAMA3, G0S2, HN1, PAK2, AFP, CYP2C9, CDH2, HAMP, SAE1, ADH6, DCN, FLJ10159, ALDH1L1, IGF1, LECT2, SLC38A1, SPARCL1, CTNNA2, GLUL, LEF1, MATN2, MME, PFN2, SPINT2, TBX3, and FGFR2. These genes correspond to the first set of genes (see Table 3) identified as useful for classifying HCC tumors into subgroups G1 to G6 as defined by their clinical and genetic features of Table 2.

In a preferred embodiment, a kit for the in vitro classification of a HCC tumor according to the invention comprises reagents for the in vitro determination of an expression profile comprising or consisting of a combination of at least 8, at least 10, at least 12, at least 14, or 16 genes selected from the group consisting of: RAB1A, REG3A, NRAS, RAMP3, MERTK, PIR, EPHA1, LAMA3, G0S2, HN1, PAK2, AFP, CYP2C9, CDH2, HAMP, SAE1, ADH6, DCN, FLJ10159, ALDH1L1, IGF1, LECT2, SLC38A1, SPARCL1.

In a more preferred embodiment, a kit for the in vitro classification of a HCC tumor according to the invention comprises reagents for the in vitro determination of an expression profile comprising or consisting of a combination of at least 8, at least 10, at least 12, at least 14, or 16 genes selected from the group consisting of: RAB1A, REG3A, NRAS, RAMP3, MERTK, PIR, EPHA1, LAMA3, G0S2, HN1, PAK2, AFP, CYP2C9, CDH2, HAMP, and SAE1.

In a still more preferred embodiment, a kit for the in vitro classification of a HCC tumor according to the invention comprises reagents for the in vitro determination of an expression profile comprising or consisting of the following 16 genes combination: RAB1A, REG3A, NRAS, RAMP3, MERTK, PIR, EPHA1, LAMA3, G0S2, HN1, PAK2, AFP, CYP2C9, CDH2, HAMP, and SAE1.

The present invention further concerns a kit for the in vitro classification of a HCC tumor between 6 subgroups from a liver HCC sample of a subject suffering from HCC, comprising reagents for the in vitro determination of an expression profile comprising or consisting of a combination of at least 8, at least 10, at least 12, at least 14, at least 16, at least 18, at least 20, at least 22, or 24 genes selected from the group consisting of: ALDH1L1, CD24, CD74, CFHR3, CYP4F12, DNAJA3, DSCR1, EPHA1, EPHB4, FAAH, FGFR2, FLJ10159, GLT8D1, HAL, MATN2, MRPS7, PAK2, PLXNB1, RAB1A, RHOQ, SLC27A5, SLPI, SMARCE1, STRA13. These genes correspond to the second set of genes (see Table 4) identified as useful for classifying HCC tumors into subgroups G1 to G6 as defined by their clinical and genetic features of Table 2.

Preferably, said kit comprises reagents for the in vitro determination of an expression profile consisting of a combination of the following 24 genes combination: ALDH1L1, CD24, CD74, CFHR3, CYP4F12, DNAJA3, DSCR1, EPHA1, EPHB4, FAAH, FGFR2, FLJ10159, GLT8D1, HAL, MATN2, MRPS7, PAK2, PLXNB1, RAB1A, RHOQ, SLC27A5, SLPI, SMARCE1, STRA13.

The present invention further concerns a kit for the in vitro prognosis of global survival and/or survival without relapse from a liver HCC sample of a subject suffering from HCC, comprising reagents for the in vitro determination of an expression profile comprising or consisting of a combination of at least 2, at least 3, at least 4, or at least 5 genes selected from the group consisting of NRCAM, PIR, RAMP3, SLC21A2, TAF9, TNA, HN1, PSMD1, MRPS7, CDC20, ENO1, HLF, STRA13, RAGD, NRAS, ARFGEF2, RAB1A, G0S2, SMAD3, DNAJA3, HELO1, RHOQ, C14orf156, NPEPPS, PDCD2, PHB, KIAA0090, IMP-3, KPNA2, KIAA0268, UNQ6077, LOC440751, G6PD, STK6, TFRC, GLA, TRIP13, SPP1, AKR1C1, AKR1C2, GIMAP5, ADM, CCNB1, TKT, AGPS, RAN, NUDT9, HRASLS3, HLA-DQA1, NEU1, RARRES2, PAPOLA, ABCB6, BIRC5, FLJ20273, C14orf109, CHKA, TUBB2, HMGB3, TXNRD1, IFITM1, KIAA0992, MPPE1, KLRB1, CCL5, SYNE1, DNASE1L3, CYP2C18, PACSIN2, PON3, and PPP2R1B.

In a preferred embodiment, the kit for the in vitro prognosis of global survival and/or survival without relapse from a liver HCC sample of a subject suffering from HCC, comprising reagents for the in vitro determination of an expression profile comprising or consisting of a combination of at least 2, at least 3, at least 4, or at least 5 genes selected from the group consisting of NRCAM, PIR, RAMP3, SLC21A2, TAF9, TNA, HN1, PSMD1, MRPS7, CDC20, ENO1, HLF, STRA13, RAGD, NRAS, ARFGEF2, RAB1A, G0S2, SMAD3, DNAJA3, HELO1, and RHOQ.

In a still more preferred embodiment, the kit for the in vitro prognosis of global survival from a liver HCC sample of a subject suffering from HCC comprises reagents for the in vitro determination of an expression profile comprising or consisting of one of the following genes combinations:

TAF9, PIR, NRCAM, and RAMP3,
TAF9, NRCAM, SLC21A2, and PSMD1,
TAF9, NRCAM, RAMP3, and PSMD1,
TAF9, NRCAM, NRAS, RAMP3, and PSMD1, or
TAF9, NRCAM, RAMP3, PSMD1 and ARFGEF2.

In a more preferred embodiment, the kit for the in vitro prognosis of global survival from a liver HCC sample of a subject suffering from HCC comprises reagents for the in vitro determination of an expression profile comprising or consisting of the following genes combination:

TAF9, NRCAM, RAMP3, PSMD1 and ARFGEF2.

In another preferred embodiment, the kit for the in vitro prognosis of survival without relapse from a liver HCC sample of a subject suffering from HCC comprises reagents for the in vitro determination of an expression profile comprising or consisting of one of the following genes combinations:

TAF9, and G0S2,
TAF9, NRCAM, and RAMP3,
TAF9, G0S2, and RAMP3,
TAF9, NRCAM, DNAJA3, and RAMP3, or
TAF9, NRCAM, G0S2, DNAJA3, and RAMP3.

In a more preferred embodiment, the kit for the in vitro prognosis of survival without relapse from a liver HCC sample of a subject suffering from HCC comprises reagents for the in vitro determination of an expression profile comprising or consisting of the following genes combination:

TAF9, NRCAM, and RAMP3.

In a kit for the in vitro prognosis of global survival and/or survival without relapse according to the invention, reagents that are provided may allow for the prognosis of only global survival or survival without relapse, or may allow for the prognosis of both global survival and survival without relapse.

In any kit according to the invention, reagents for the determination of an expression profile may include any reagent useful for the determination of a gene expression level. Said determination of the expression level may be carried out at the proteic or nucleic level.

Reagents suitable for the determination of an expression profile at the proteic level include, without being limited to, antibodies and antibody fragments, reagents for mass spectrometry analysis, and protein microarrays.

Conversely, reagents suitable for the determination of an expression profile at the nucleic level include, without being limited to, amplification primers, nucleic probes and nucleic acid microarrays.

In particular, in a kit for the classification of HCC comprising reagents for determining an expression profile involving genes of the first set of genes useful for HCC classification (see Table 3), said kit may advantageously comprise amplification primers, and optionally nucleic probes useful for quantitative PCR analysis of gene expression. Said kit may also optionally contain other useful quantitative PCR reagents.

Alternatively, in a kit for the classification of HCC comprising reagents for determining an expression profile involving genes of the second set of genes useful for HCC classification (see Table 4), said kit may advantageously comprise a nucleic acid microarray, and optionally other reagents useful for microarray analysis of gene expression.

In addition, in any kit according to the invention, said reagents may be provided with instructions for performing a method of in vitro classification or prognosis of global survival and/or survival without relapse according to the invention. For instance, the said instructions may either
1) allow to the user himself to perform the classification or prognosis, for instance by giving the necessary formulas and various parameters values, or
2) instruct the user to enter its expression data into a dedicated software that may be provided in the kit or may for instance be accessible on the internet.

In this case, the reagents and instructions may be provided together in the same package or separately in two distinct packages.

The invention further concerns a method of treatment of a subject suffering from HCC, comprising:
a) determining a global survival and/or survival without relapse from a liver HCC sample of said subject according to a method of the invention, and
b) administering to said subject an adjuvant therapy in the presence of a bad prognosis, while not administering such an adjuvant therapy in the absence of a bad prognosis.

The invention also concerns a method of in vitro screening of compounds useful for the treatment of one of the 6 HCC subgroups according to the invention, comprising:
a) providing HCC tumor samples,
b) classifying said HCC tumor samples according to a method of the invention, and
c) testing the ability of said compounds to inhibit the in vitro growth of the HCC tumor samples that have been classified in said HCC subgroup.

The invention further concerns a method of treatment of a subject suffering from HCC, comprising:
a) classifying said subject HCC tumor sample into one of the 6 subgroups according to the invention, and
b) administering to said subject a therapeutic treatment targeted to the HCC subgroup to which it HCC tumor sample belongs.

Having generally described this invention, a further understanding of characteristics and advantages of the invention can be obtained by reference to certain specific examples and figures which are provided herein for purposes of illustration only and are not intended to be limiting unless otherwise specified.

DESCRIPTION OF THE FIGURES

FIG. 1. Schematization of the different HCC subgroups defined by transcriptome analysis with their related clinical, genetic and pathways.

G1 to G6 indicates the HCC subgroups of tumors defined by transcriptome analysis. Vertical lines indicate significant associated features (see Table 1). LOH, loss of heterozygosity; Hemochrom, hemochromatosis; AFP, alpha-fetoprotein, HBV, hepatitis B virus. Solid and dotted lines underlining words indicate primarily over- and under-expressed genes in that particular functional category, respectively.

Figure 2:
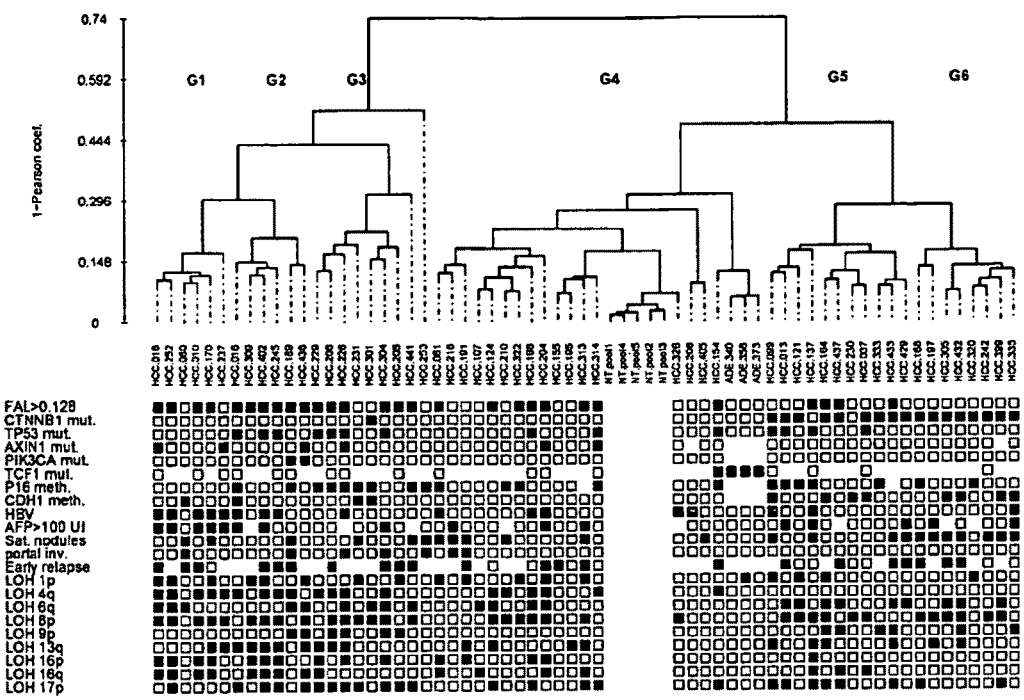

FIG. 2. Unsupervised hierarchical clustering.

The dendrogram shown was obtained based on the expression profile of 6,712 probe sets of Affymetrix data from 57 HCC tumors, 3 adenomas and 5 pools of non-tumor tissues using Ward's linkage and 1-Pearson correlation coefficient. Clinical and genetic features are indicated in black and white boxes when positive and negative, respectively. In case of HBV infection, grey boxes indicate low number of viral DNA copies. FAL indicates Fractional Allelic Loss (black indicates tumors containing the deletion of more than 5 chromosome arms (FAL>0.128)). Other abbreviations are as follows: CTNNB1, β-catenin gene; Mut, mutation; meth, methylation; sat. nodules, satellite nodules at less than 1 cm from the principal tumor; AFP, Alpha-fetoprotein; CDH1, E-cadherin gene; portal inv., portal invasion.

FIG. 3: Characterization of a selected number of HCC subgroup G1 specific genes using QRT-PCR.

a. Validation of genes specifically over-expressed in HCC predicted subgroup G1. IGF2 (Insulin Growth Factor 2), AFP (alpha feto protein), SOX9 (sex determined region Y-box9), MYH4 (Myosin heavy chain IIb), PEG1 and PEG3 (Paternally expressed 1 and 3) were analysed in 109 HCC. Box-plots show (extending from $25^{th}$ percentile to the $75^{th}$ percentile with a line at the median ($50^{th}$ percentile) the range of relative (tumor versus the mean of 21 non-tumor (T/NT)) $\log_{10}$ expression values obtained for the indicated gene in each of the 6 predicted subgroups (G1 to G6), in 21 non-tumor samples (NT) and in 19 fetal liver samples (FL). The whiskers extend above and below the box to show the highest and lowest values. The P values from ANOVA tests comparing the expression values in the different HCC subgroups are indicated below the gene symbol.

b. Validation of genes over-expressed in PIK3CA mutated tumors (PIK3CA mut) compared to 107 non-mutated HCC (PIK3CA NM) for EEF1A2 (eukaryotic translation elongation factor 1 alpha) and PRSS7 (enterokinase precursor). Resulting P values from a t-test comparing mutated and non-mutated samples are shown below the gene symbol.

FIG. 4: Characterization of HCC tumors leading to G5 and G6 subgroups.

a. Validation of genes specially over-expressed in HCC predicted subgroup G5 and G6 using QRT-PCR. Box-plots representing the range of relative (tumor versus mean of non-tumor (T/NT)) log 10 expression values obtained for GLUL (glutamine synthase), TBX3 (transcription factor TBX3), MME (membrane metallo-peptidase, CD10), LAMA3 (alpha-3 chain of laminin 5), SPARCL1 (hevin), MERTK (c-mer proto-oncogene tyrosine kinase), PAP (Pancreatitis associated protein), EPHB2 (ephrin receptor B2), LEF1 (lymphoid enhancer-binding factor 1) and CDH1 (E-cadherin) analyzed in 109 HCC samples as described in FIG. 3.

b. β-catenin immunostaining in representative cases of HCC mutated for β-catenin and leading to G5 and G6. In case HCC303 (G5), note a low number of stained nuclei and an intense staining of the plasma membrane (white arrows). In case HCC305 (G6), cytoplasm and nuclei of hepatocytes are intensively stained (black arrows) without signal at the plasma membrane.

c. Protein expression of E-cadherin in HCC of G6 using western blot (upper panels) compared to mRNA level of expression (group G5 and G6) using QRT-PCR (lower panel).

Figure 5A:
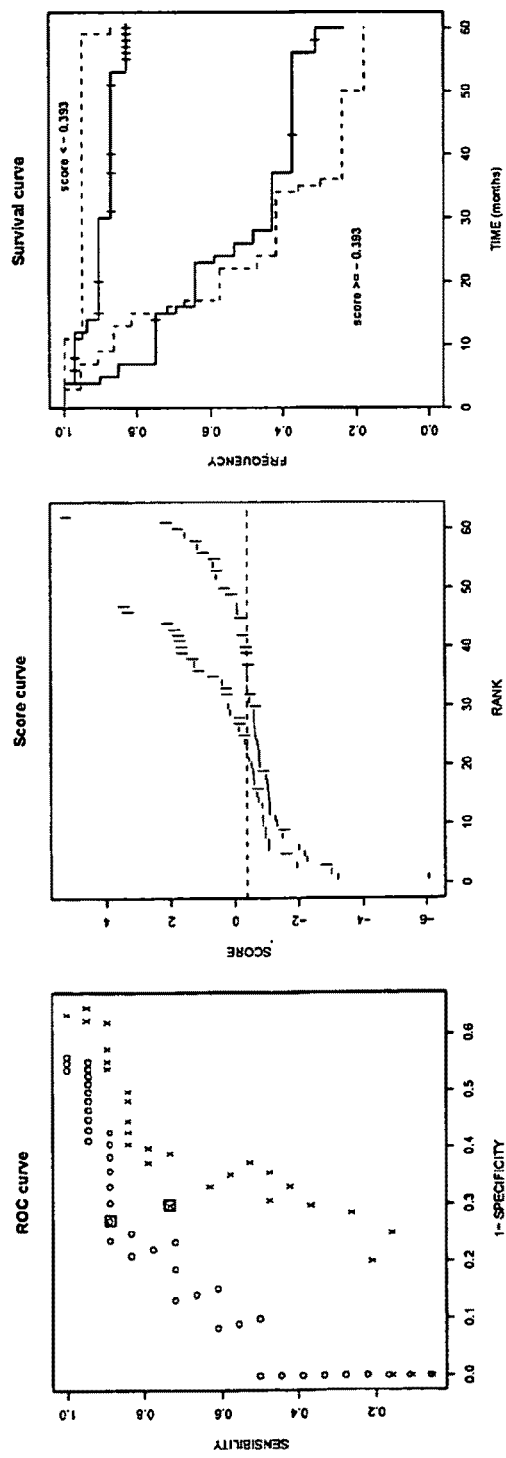

FIG. 5: Predictors of survival a. Results for overall survival best predictor are shown. The ROC curve gives the specificity and sensibility for different score thresholds. Circles correspond to the training set (n=42) and crosses to the validation set (n=53). Squared circle and cross indicate the sensibility and specificity obtained for the chosen threshold (−0.393). Threshold was chosen in order to have a maximal success rate and a minimal P-value based on the Fisher exact test for the "predicted class/true class" contingency table of the training set samples. The Score curve shows the scores obtained for training set (upper curve) and validation set (lower curve) from the global survival score formula described in Example 3.2 with the parameters of Table 11, while the dotted line indicates the chosen threshold score. Horizontal strokes represent alive patients while vertical strokes represent dead patients. Survival curves for training set (dotted lines) and validation set (solid lines) are stratified by the indicated score threshold.

b. Results for the best disease free survival predictor, are shown. The same representation code as in FIG. 5a is used. The Score curve shows the scores obtained from the disease-free score formula described in Example 3.2 with the parameters of Table 14. Horizontal strokes represent free of disease patients while vertical strokes represent not free of disease patients.

EXAMPLES

Example 1

Strategy of Transcriptional Analysis of HCC Tumors

Tumors and Samples, Clinical Data

A series of 120 hepatocellular carcinomas and 3 hepatocellular adenomas with their corresponding non-tumor tissues were collected from 123 patients treated by liver resection in three French surgical departments from 1992 to 1999. For all cases included in this study, full clinical data and follow up were available. All these tumors were clinically characterized as previously described (Laurent-Puig, P. et al. *Gastroenterology* 120, 1763-73 (2001)). The sex ratio (M:F) was 1:4 and the mean age of the patients was 60 years (median age=63 years, range from 18 to 85). The patients were born in France (92 cases), sub-Saharan Africa (11 cases), the Mediterranean area (7 cases), the Antilles (4 cases) and Asia (4 cases). Risk factors for HCC of hepatitis B virus, hepatitis C virus, alcohol abuse, and hemochromatosis occurred in 36, 30, 40 and 6% of the tumors, respectively. In 25 cases HCC were developed in the absence of known risk factor and in 16 cases at least two risk factors were found. The histological grade of tumor differentiation was assigned according to the Edmondson and Steiner grading system, grade I (7%), II (49%), III (39%) and IV (4%). In 103 cases the preoperative α-fetoprotein serum level was available and over 100 IU/ml for 37 patients. Macroscopic and/or microscopic vascular invasion was recorded in 37% of the cases. Satellite tumors defined by nodule(s) found at less than 1 cm from the main tumor was recorded in 41% of the cases. Overall and disease-free survival was assessed in 99 patients with a R0 complete resection after eliminating patients treated by liver transplantation or died within a 3 months post-operative period. To minimize the effect of the occurrence of a second unrelated tumor in cirrhosis, we did not take into account survival data after 5 years. The mean follow-up in whole series was 38 months (range 3-60 months) and it was 49 months for patients still alive. Two qualitative prognosis variables were constructed: (1) "early-relapse" yes or no was defined by the presence of tumor-relapse within the two years after liver resection and the lack of relapse during the 4 post-operative years; (2) "early-death" yes or no was defined by the occurrence of death within the 3 years after liver resection and the lack of death during the 5 post-operative years. For the Affymetrix analysis, 5 pools of 3 non-tumor liver tissues matching the analyzed tumors were used including alcoholic cirrhosis (pool 1), alcoholic non-cirrhotic liver (pool 2), HBV non-cirrhotic liver (pool 3), HCV cirrhosis (pool 4) and HBV cirrhosis (pool 5). In the QRT-PCR experiments, these 15 non-tumors RNAs and 6 additional normal non-tumor liver RNAs were individually analyzed. 19 human fetal liver samples at different stage of pregnancy (ranging from 11 to 29 weeks of pregnancy) were also collected. The study was approved by the local Ethics Committee (CCPPRB Paris Saint-Louis), and informed consent was obtained in accordance with French legislation.

Basic Transcriptome Analysis

Microarray analyses were performed using 5 µg of total RNA of each sample as starting material and 20 µg cRNA per hybridization (GeneChip Fluidics Station 400) of HG-U133A Affymetrix GeneChip™ arrays. Images from each array were generated using HP GeneArray 2500 and analyzed following the manufacturer's protocols Except when indicated, all transcriptome analysis was carried out using either an assortment of R system software (v1.9.0) packages including those of Bioconductor (v1.1.1) or original R code. R packages and versions are indicated when appropriate. Raw feature data from 65 Affymetrix HG-U133A GeneChip™ microarrays were normalized and $\log_2$ intensity expression summary values for each probe set were calculated using robust multi-array average (package affy V1.4.32). Probe sets corresponding to control genes or having a "_x_" annotation were masked yielding a total of 19,787 probe sets available for further analyses.

Example 2

Classification of HCC Tumors 2.1 Material and Methods

Gene Mutations, Chromosome Imbalance, Quantification of HBV Genome and DNA Methylation For all samples, tumor and non-tumor DNAs were dissected and stored at −80° C. until DNA and RNA extraction using Qiaquick and Rneasy extraction kits, respectively (Qiagen). DNAs were quantified by fluorometry (Fluoroskan Thermo Lab-system), RNA were quantified using a spectrophotometer at 260 nm (Nanodrop). The quality of DNA and RNA was controlled by gel electrophoresis followed by staining with ethidium bromide and Agilent 2100 bioanalyser. RNAs were qualified if the 28S/18S ratio was more than 1.5 for Affymetrix experiments and more than 1 for quantitative RT-PCR analyses. Gene mutations were searched in TP53 exons 2 to 11, CTNNB1 coding for β-catenin exon 2 to 4, AXIN1 exon 1 to 10, PIK3CA exon 1 to 20, by direct sequencing tumor DNAs using a 3100 Applied Biosystems sequencer. Allelic losses and chromosome imbalance were searched by genotyping 400 markers from LMS2 microsatellites panel (Applied Biosystems) as previously described (Laurent-Puig, P. et al. *Gastroenterology* 120, 1763-73 (2001)). For all samples related to HBV infection either by serological results or viral DNA amplification (Laurent-Puig, P. et al. *Gastroenterology* 120, 1763-73 (2001)), HBS and HBX copies of DNA were quantified in tumor and non-tumor DNAs using Syber green method (Applied Biosystems). Sequences of HBS and HBX DNA were determined in all tumors to ensure that primers used for quantification were chosen in regions outside viral polymorphisms or mutation. Quantification of viral DNA were related to a chromosome 22 PCR amplification. Efficacy of PCR amplification was measured at 95, 97 and 94% for HBS, HBX and chromosome 22 reference, respectively. Tumor and non-tumor DNA samples were also carefully quantified using fluorimetry with Hoechst and concentrations were checked by agarose gel electrophoresis. A low number of viral DNA copies in tumors was defined by a ratio HBX/reference and HBS/reference inferior to 0.5 (mean: 0.01, range: 0.002-0.5, standard error: 0.14). A high number of viral DNA copies in tumors was defined by a ratio HBX/reference and HBS/reference superior to 1.5 (mean: 25, range: 1.6-212, standard error: 46). No value was found between 0.5 and 1.6. DNA methylation at CDH1 and CDKN2A promoter was searched using bisulfite DNA and methylation specific amplification as previously described (Lee, S. et al. *Am J Pathol* 163, 1371-8 (2003); Zochbauer-Muller, S. et al. *Cancer Res* 61, 249-55 (2001)).

Quantitative RT-PCR Analysis

For quantitative RT-PCR analyses, 3 µg of total RNA was reverse transcribed using the High capacity Archive kit and random hexamers (Applied Biosystems). For each sample and tested gene, 1 µl of cDNA corresponding to 2 ng of reverse transcribed RNA, were analyzed by TaqMan PCR analysis, in duplicate, using TaqMan® Low Density Array and the ABI PRISM® 7900HT System (Applied Biosystems). The quality of cDNAs was assessed using a R18S quantification by real time PCR (coefficient of variation 7% for the entire series). The relative amount of the tested mRNA in samples, was determined using the $2^{-\Delta\Delta CT}$ method where $\Delta\Delta CT=(CT_{TESTED}-CT_{R18S})_{sample}-(CT_{TESTED}-CT_{R18S})_{calibrator}$ (Livak, K. J. & Schmittgen, T. D. *Methods* 25, 402-8 (2001)). Briefly, expression results of a gene were normalized to internal control ribosomal 18S and relatively to a calibrator, consisting in the mean expression level of the corresponding gene in non-tumor samples normalized to internal control ribosomal 18S. The values given in tables and graphs express the n-fold ratio of the gene expression in a tested sample compared to the mean of non tumor tissues.

Western Blot and Immunohistochemistry

Frozen tissues were homogenized with a Dounce in 500 µl ice-cold RIPA Lysis buffer (Santa Cruz) and protein concentration was determined by BCA protein assay kit (Pierce). Immunoblot analysis was performed using 50 µg of proteins migrated on a SDS 6% polyacrilamide gel, a polyclonal E-cadherin antibody (SC-7870, 1:500, Santa Cruz), a peroxidase-conjugated secondary antibody (1:2000, Santa Cruz) and enhanced chemoluminescence (ECL, Pierce). Immunostaining was performed on 5 µm sections of formalin-fixed, paraffin-embedded liver samples, using monoclonal anti-β-catenin (1:400, BD Biosciences 610153), biotinyled anti-mouse (1:200, Vector Laboratories BA-2000), Vectastain ABC Elite standard kit (Vector Laboratories PK-6100), DaB kit (Vector Laboratories SK-4100). Prior to immunostaining endogenous peroxidase was blocked and antigen retrieval was performed with 0.001M citrate buffer pH 7 in a pressure cooker (Biogenex).

Classification Based on Transcriptome Analysis

The classification of the 65 samples was based on a series of 24 hierarchical cluster analyses, obtained from 8 data subsets and 3 different linkage methods (average, complete and Ward's), using 1-Pearson correlation as a distance metric (package class V 7.2-2). The 8 data subsets corresponded to 8 unsupervised selections of the most varying expression profiles. Criteria for this selection were the significant difference of the variance for a given probe set compared to the median variance (P<0.01), as well as different "robust" coefficient of variation thresholds (rCVs, calculated by dividing the standard deviation by the mean of a probe set log 2 intensity values for n-2 samples eliminating the lowest and highest values). Between 99 and 6,712 probe sets were selected (99.5th and 60th rCV percentiles). The stability of the initial 24 dendograms was assessed by comparing each one to cluster results obtained after perturbation/resampling (100 iterations for each, see supplemental information for details on the stability score). The model was also tested using an k-means clustering approach, with different initial number of clusters (k=7 . . . 15). Using the best run out of 200 for each k (i.e. the one with the maximal distance between the k groups), samples were consistently grouped according to or as subsets of the 6 HCC subgroups.

Association of HCC Subgroups and Clinical/Genetic Variables

Fisher exact tests were carried in order to determine the significance of the association between different clinical and genetic variable and the 6 HCC tumor subgroups. Cluster results obtained from all combinations of linkage methods and gene lists were tested. In addition, variables with multiple modalities (e.g. HBT) were recoded into binomial values and each combination was tested. For the global predictor using the QRT-PCR results (see Table 1), 1,000 random permutations of class labels were used to correct the original P values which means that a P of 0 in the table equates to P<0.001.

Construction of a Global Predictor

Affymetrix Data Predictor

To build a multi-class predictor, the 65 samples were divided into a training set (n=36, 6 for each cluster group, randomly selected), and a test set (n=24 tumors plus 5 non-tumor samples). A six steps learning strategy was then used: (1) gene supervised selection using F-tests and based on the training samples (n=376 probe sets); (2) gene probe set filtering based on sub-sampling, on overall intensity levels and redundant HUGO gene symbols and false discovery rate control (n=258); (3) random sub-selections of 8-25 genes, segmented (or not) by gene cluster bins; (4) rule learning using 5 prediction algorithms; (5) rule selection based on success rate of predicting the test set; (6) rule validation using RT-PCR data and Fisher exact tests to assess the association between clinical and genetic factors to predicted groups.

More precisely, the different steps were performed as follows:

1. Gene selection and 2. gene probe set filtering: using S1, we performed an F-test using a multivariate permutation test based on 1000 permutations of sample labels to correct for multiple testing (BRB ArrayToolsv3.0.beta2). This test yielded 1,041 probe sets that contained less than 10 false discoveries. We performed the same test on a sub-selection of 18 samples in S1 (3 randomly selected cases per group) and found 515 significant probe sets (here a p value<0.001 was used as the threshold criteria due to the low number of samples per class which renders the permutation test unreliable). The intersection of these two lists and filtering out probe sets that had a maximal intensity less than 100 units in all 6 HCC cluster groups yielded 258 probe sets. For the probe sets corresponding to the same HUGO gene symbol, we kept one probe set per symbol by eliminating probe sets having a lower F statistic reducing the list to 225 probe sets.

3. Random sub-selections of genes: (i) Starting from the 225 probe sets list, we generated, at random, 1000 sub-lists of k number of probe sets (k=8 . . . 25) per list (total of 18,000 sub-lists). (ii) From the 225 probe sets list, we generated 1,000 sub-lists of k number of probe sets (k=15, 30, total of 2,000 sub-lists), by choosing the same proportion of genes from individual gene-cluster bins. Gene-cluster bins were constructed based on complete linkage clustering of the 225 probe sets (using 1-Pearson coefficient as the distance metric), and then cutting the dendrogram to yield 15 cluster nodes (n=4 to 49 probe sets by cluster bin); (iii) We also generated 1,000 sub-lists of k probe sets (k=8, 16, 24, a total of 3,000 sub-lists) equally representing gene-cluster bins derived from an average linkage clustering, (1-Pearson coefficient) and cutting the dendrogram into 20 nodes, merging small cluster nodes (represented by less than 10 probe sets or a correlation higher than 0.3 with closest neighboring node) yielding a total of 8 major gene-cluster bins (n=9–87 probe sets by cluster bin).

4. Rule learning: The expression data from the set S1, restricted to the 23,000 sub-lists of probe sets, served to train 5 prediction algorithms (SVM (e1071, v1.4-1), PAM (pamr, v1.14.2), k-NN (class, v7.2-2), DQDA and DLDA (sma, v0.5.14)), yielding 115,000 predictors.

5. Rule selection: For each algorithm, in combination with each value of k((i)k=8 . . . 25; (ii)k=15,30; (iii) k=8, 16, 24), we selected the best sub-list among 1,000, based on success rate of the corresponding predictor (trained with training set) to classify validation set samples (in case of equality the first sub-list encountered was kept); this selection gave 115 predictors. Among those, 7 predictors, related to 6 distinct sub-lists, gave a success rate to classify samples from the validation set higher than 93%. We selected the 24 genes sub-list related to 2 predictors (algorithms SVM and PAM) among those 6 sub-lists. We observed that this sublist had a success rate of 97% using Nearest Shrunken Centroids (PAM) of predicting true class membership of the 36 samples in the training set (100% for SVM) and 93.1% of the 29 samples in the validation group.

6. Rule validation: RT-PCR data were obtained for 23 out of the 24 genes in the previously selected sub-list (no primers were available for CD24), along a series of 109 tumors, including 46 samples previously analysed with Affymetrix HG-U133A GeneChip™ microarrays (28 in the original training set (S1a), and 18 HCC in the original validation set (S2a)). Using ΔCt data (with 18S as control gene) for the set S1a, we trained 5 prediction algorithms (SVM, PAM, k-NN, DQDA and DLDA): applied to set S2a, the predictor derived from SVM yielded 81% success rate (100% for S1a).

PCR Data Predictor

Given the partial success of the 24 genes predictor transferred from Affymetrix data to PCR data, a new predictor was searched, starting the process from an initial list of 103 genes among the 140 genes analyzed by QRT-PCR. These 103 genes corresponded to the supervised statistical tests comparing the different cluster groups, using all 65 samples in the Affymetrix data set. The same learning strategy was then followed as described for Affymetrix data: random sub-selections of genes; rule learning; rule selection; rule validation. At random, 500 sub-lists of k number of probe sets (k=5 . . . 16) per list (total of 6,000 sub-lists) were generated. Using ΔCt data (control gene 18S), 5 prediction algorithms (SVM, PAM, kNN, DQDA, DLDA) were trained on set S1 and obtained 30,000 predictors. For each algorithm, in combination with each value of k, the best sub-list among 500 was selected, based on success rate of the corresponding predictor (trained with set S1) to classify test set S2 (in case of equality the first sub-list encountered was kept); this selection gave 60 predictors. Among those, 3 predictors gave the highest success rate to classify test set S2, one of which, yielded a success rate (of S2) higher than 88% for 3 different algorithms, and was therefore considered as the best. This predictor was obtained with DLDA algorithm, and predicted set S1 with 100% success rate and set S2 with 94% success rate. As a validation of the selected predictor, the relevance of predicted classes for set S3 was assessed via the P-value of a Fisher exact test measuring the level of association between predicted classes (1,2,3 vs 4,5,6) and FAL (P=8.5 $10^{-4}$), as well as between predicted classes (4 vs 5,6) and CTNNB1 mutation (P=5 $10^{-5}$).

Determination of the Specific HCC Subgroup Differentially Expressed Genes and Subsequent GO Analyses All univariate t and F tests were performed using BRB ArrayTools (v3.2 b5) on the log 2-transformed intensity values for the 19,787 probe sets. A nominal significance level of each univariate test of P<0.001 as well as 90% confidence of less than 10 false discoveries was designated based on a multivariate test using 1,000 permutations. All inter-group t-tests were performed to identify genes that were found to be differentially expressed between a given subgroup (or a combination of subgroups) and the remaining samples (Gx versus Gnon-x) as well as the between 5 pooled non-tumoral samples (Gx versus non-tumoral). Genes that were found by both types of tests for a given subgroup (and not between any other group comparison) as well as being significant (P<0.001, less than 10 false discoveries as described) in an ANOVA analysis (F test described above) were considered to be a HCC subgroup (or combination of subgroups) specific gene.

Stability Assessment of Classification

For the perturbation, random Gaussian noise ($\mu$=0, $\sigma$=1.5× median variance calculated from the data set) was added to a given data set. Each dendrogram was partitioned into k groups (k=2 . . . 18) and the proportion of sample-pair retained in each group compared to the initial dendrogram was used as a stability score (score ranges from 0 and 1 where a score of 1 means the perturbation (or resampling) had no effect on the membership of the cluster group).

2.2 Results

Non-Supervised Transcriptome Analysis Defines Clusters of Tumors Closely Associated with Clinical and Genetic Alterations Fifty-seven HCC, 3 hepatocellular adenomas and 5 samples of pooled non-tumor tissues were analyzed using Affymetrix HG-U133A GeneChip™ arrays. Based on a non-supervised analysis we have developed a robust model of HCC classification that partitions HCC tumors into 6 subgroups (FIG. 2) each of which are highly associated with clinical and genetic factors based on Fisher exact tests (see above Tables 1 and 2). Based on the conducted analysis, the 60 tumor samples are sub-divided into 2 major groups each being further subdivided into 3 smaller subgroups (named here G1 to G6). This classification was found to be extremely robust when confronted with perturbation/resampling tests (mean reproducibility scores for each cluster analysis was found to be at least 0.9 for the 2 major groups and the 6 subgroups) as well as consistent with an iterative k-means cluster analysis (see Materials and Methods). Moreover the topology of the sample partition was conserved across different gene lists and cluster linkage methods. The two major groups correspond to chromosome instable (G1, G2 and G3) and stable (G4, G5 and G6) samples since G1 to G3 showed significant higher fractional allelic loss (FAL) than G4 to G6 ($P<10^{-3}$, Table 2). In addition HCC belonging to G1 to G3 groups were slightly related to early relapse and early death compared to HCC from G4 to G6 (P=0.05, Table 2). The different subgroups were characterized by TP53 mutations (G2 and G3), an HBV infection (G1 and G2), with low number of HBV DNA copies (G1) and CTNNB1 gene mutations (G5 and G6). The presence of distant cancerous nodules found less than 1 centimeter away from the primary tumor was associated with G6 (P=0.04, Table 2), indicating a high potential of local invasion of these tumors. The 5 sample-pools of non-tumor liver tissues clustered tightly together and was found within a large, heterogeneous group (G4) containing 20 tumors, four of which, in the same small cluster, had TCF1 mutations (3 adenomas and one HCC).

Identification of 2 Predictors of the 6-Groups Classification

Given the clinical relevance of the subgroups and the diagnostic potential of this classification, the inventors' aim was to identify a class-predictor more adapted to a clinical environment by using the more time and cost efficient technology quantitative reverse-transcriptase PCR (QRT-PCR). In order to search for genes that can predict class membership to the 6 HCC subgroups a predictor was first constructed using the Affymetrix data (see material and methods and following Table 10). This analysis identified a first 24-gene predictor (ALDH1L1, CD24, CD74, CFHR3, CYP4F12, DNAJA3, DSCR1, EPHA1, EPHB4, FAAH, FGFR2, FLJ10159, GLT8D1, HAL, MATN2, MRPS7, PAK2, PLXNB1, RAB1A, RHOQ, SLC27A5, SLPI, SMARCE1, STRA13) yielding a high success rate of class prediction using Affymetrix data (93.1%) but proved less satisfactory using QRT-PCR data (81%).

TABLE 10

List of the 24 genes that were identified as the global HCC predictor for the Affymetrix samples using the Affymetrix data. Included are the HUGO gene symbol, the F-statistic from an ANOVA between all 6 classes of samples and associated geometric mean of non-log intensity values per HCC sub-group (G1-G6).

| Gene HUGO Symbol | F statistic | G1 | G2 | G3 | G4 | G5 | G6 |
|---|---|---|---|---|---|---|---|
| ALDH1L1 | 13.1 | 221 | 226 | 766 | 993 | 2213 | 2123 |
| CD24 | 10.7 | 511 | 235 | 274 | 66 | 75 | 17 |
| CD74 | 5.7 | 1343 | 2008 | 2481 | 1896 | 1121 | 4973 |
| CFHR3 /// CFHR4 | 5.8 | 368 | 1000 | 174 | 2527 | 1567 | 980 |
| CYP4F12 | 8.4 | 341 | 347 | 243 | 461 | 595 | 459 |
| DNAJA3 | 6.8 | 412 | 521 | 621 | 662 | 727 | 658 |
| DSCR1 | 5.5 | 139 | 134 | 136 | 205 | 170 | 265 |
| EPHA1 | 16.2 | 432 | 972 | 189 | 530 | 230 | 120 |
| EPHB4 | 9.3 | 538 | 264 | 204 | 261 | 288 | 220 |
| FAAH | 5.6 | 140 | 134 | 127 | 258 | 169 | 186 |
| FGFR2 | 20.8 | 373 | 515 | 71 | 47 | 25 | 29 |
| FLJ10159 | 11.9 | 896 | 289 | 168 | 116 | 89 | 40 |
| GLT8D1 | 8.5 | 471 | 433 | 463 | 542 | 933 | 868 |
| HAL | 27.7 | 380 | 1065 | 139 | 298 | 83 | 66 |
| MATN2 | 10.4 | 291 | 180 | 114 | 190 | 60 | 37 |
| MRPS7 | 6.5 | 321 | 389 | 725 | 403 | 438 | 448 |
| PAK2 | 7.6 | 297 | 199 | 337 | 143 | 150 | 119 |
| PLXNB1 | 6.9 | 482 | 343 | 194 | 207 | 304 | 217 |
| RAB1A | 6.5 | 1960 | 2490 | 2388 | 1820 | 1601 | 1722 |
| RHOQ | 5.2 | 220 | 389 | 366 | 259 | 191 | 204 |
| SLC27A5 | 12.2 | 282 | 564 | 437 | 2309 | 2147 | 2152 |
| SLPI | 18.0 | 1148 | 2766 | 313 | 1829 | 159 | 141 |
| SMARCE1 | 7.3 | 439 | 395 | 489 | 265 | 303 | 253 |
| STRA13 | 13.7 | 433 | 570 | 1170 | 583 | 959 | 1151 |

Thus, a series of supervised tests using Affymetrix data and relevant clinical and genetic annotations (i.e. the mutational status of TP53, CTNNB1 and AXIN1 genes, presence and titer of HBV, early relapse and overall survival) was performed. A list of 140 genes was assembled that were shown to be significant in one or more of these supervised tests. All but five of these selected genes were validated by QRT-PCR in 109 HCC tumors (including 46 among the 57 HCC analyzed using Affymetrix microarrays and a validation set of 63 HCC) and 21 non-tumor liver tissues. A high correlation between the Affymetrix data and the QRT-PCR data was found with 135 out of the 140 selected genes (Spearman's rho median correlation coefficients of 0.84 using ΔCt values). Using the QRT-PCR data, multiple sub-lists of a subset of 103 genes (among the 135 tested) were tested genes in order to identify the best global predictor of the 6 HCC subgroups. For this purpose, the 46 HCCs analyzed with Affymetrix microarrays were divided into a training (n=28) and test set (n=18). All genes listed in the previously described Table 3 were at least shown to be significant in one or more of these supervised tests, and most of them were present in at least one or two good classification predictors. The best success rate of predicting true class membership of the training set (100%) and test set (94.4%) was obtained with the Ct values of 16 genes (RAB1A, PAP, NRAS, RAMP3, MERTK, PIR, EPHA1, LAMA3, G0S2, HN1, PAK2, AFP, CYP2C9, CDH2, HAMP, SAE1) using the DLDA prediction algorithm.

The best predictor follows the following formulas:

$$\text{Predicted class }(sample_i) = \arg\min_{k=1\ldots 6}(\text{Distance}(sample_i, class_k)),$$

wherein $$\text{Distance}(sample_i, class_k) = \sum_{t=1\ldots 16} \frac{(\Delta\exp(sample_i, gene_t) - \mu(class_k, gene_t))^2}{\sigma(gene_t)},$$

and wherein the different $\mu(class_k, gene_t)$ and $\sigma(gene_t)$ parameters are those listed in the already described Table 5.

Thus, after having calculated the distance between the given sample and the centroïd representation of each class, the new sample is affected to the closest class.

This signature was then used to partition the 63 samples of the validation tumor set into 6 subgroups. As observed in the first set of tumors analyzed in Affymetrix experiment, significant associations, using Fisher exact tests, were found between FAL, TP53, HBV infection and CTNNB1 gene mutation and the different predicted subgroups, as well as with those using the complete series of 109 HCC tumors (Table 1).

Figure 3A:
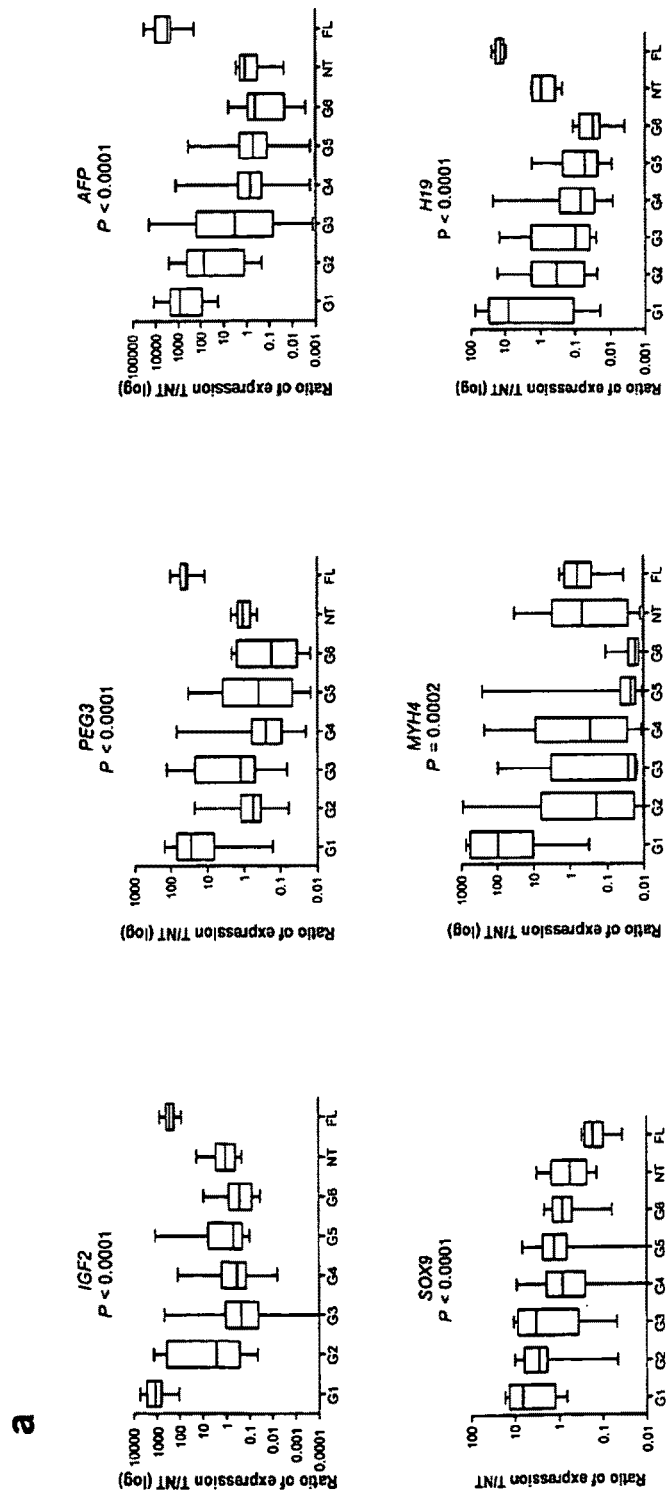
Figure 3B:
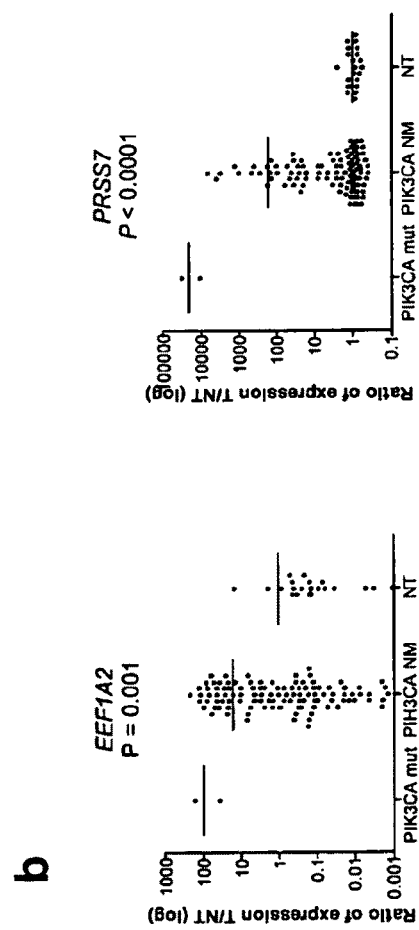

Identification of Key Signaling Pathways and Functional Categories of Genes Implicated in Each HCC Subgroup To identify key pathways affected in the different HCC subgroups 1,560 genes specifically deregulated in one or more HCC subgroups were identified based on the results from an all group-wise t-test analysis combined with ANOVA. For all lists of genes specific of HCC subgroups, association of genes in known pathways was also searched for. An enrichment of cell cycle/proliferation/DNA metabolism genes specifically over-expressed in subgroups G1 to G3 was observed, corresponding to chromosome instable samples (P<0.01). A high number of genes specifically over-expressed were observed for the G1 subgroup (related to HBV infection with a low number of viral DNA, AXIN1 mutations, a younger age, a high sera level of AFP and frequent origin from Africa, Tables 1 and 2). Among them, genes encoding for proteins expressed during development were found: myosin heavy chain IIb, MYH4, the transcription factors SOX9 and SOX4, and parentally imprinted genes: insulin like growth factor 2 (IGF2), paternally expressed gene 1, 3 and 10 (PEG1, PEG3 and PEG10), alpha-fetoprotein (AFP) and sarcoglycan epsilon (SGCE). The differential expression of all these genes was validated using QRT-PCR on 109 tumors (FIG. 3a). The imprinted genes tested were highly over-expressed in normal fetal livers (FIG. 3a). H19 mRNA was also over-expressed, not only in G1 samples but also in fetal samples, correlating with IGF2 in these two groups ($R^2$=0.4 and 0.6, respectively).

Subgroup G2 tumors (related to HBV infection with a high number of viral DNA copies, frequent local and vascular invasion and TP53 mutations) were significantly associated with over-expression cell cycle/proliferation/DNA metabolism genes (P<0.01), an enrichment that was equally observed in G3 (related to TP53 mutations and CDKN2A promoter methylation) and all chromosome instable samples (P<0.007). A significant over-representation of over-expressed genes implicated in protein phosphorylation was also identified (P<0.009). Interestingly, mutations in the PIK3CA gene predicted to result in the activation of the phosphatidylinositol 3-kinase (PI3K)-AKT pathway were identified in two tumors belonging to G2. These two samples were closely associated in the non-supervised clustering analysis (FIG. 2). 38 genes specifically over-expressed in the PIK3CA mutated samples were identified when compared with the other tumors in groups G1 to G3. Among these genes, the over-expression of two genes coding for the protein elongation factor EEF1A2 and the enterokinase PRSS7 was validated, which are specifically over-expressed in PIK3CA mutated tumors using QRT-PCR (P=0.001, FIG. 3b). Furthermore, GO analysis demonstrated an enrichment of cell communication genes in PIK3CA mutated tumors (P=0.07).

Figure 4A:
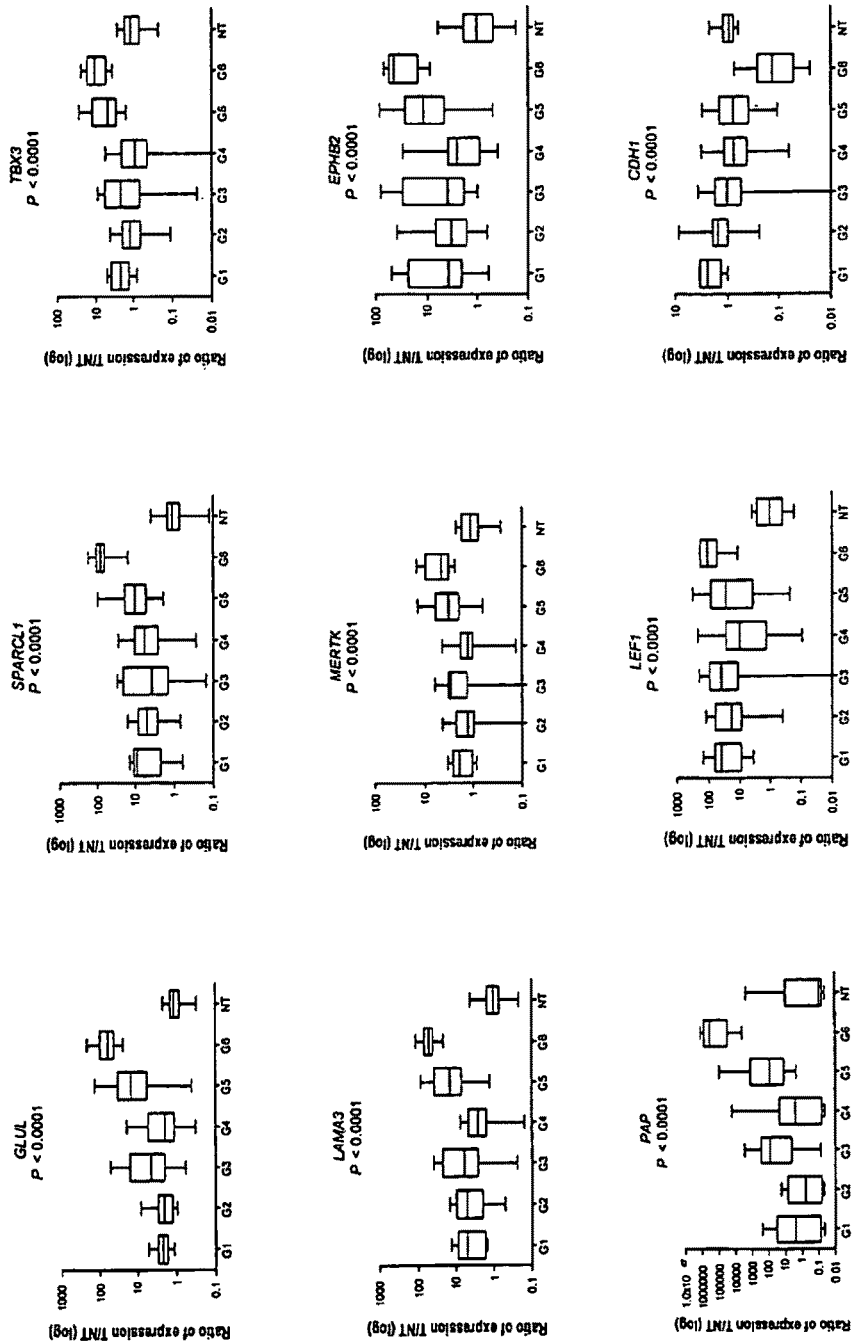
Figure 4B:
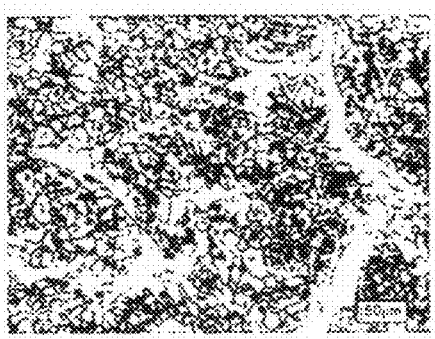
Figure 4B:
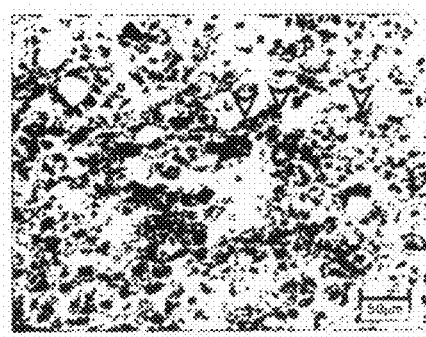
Figure 4C:
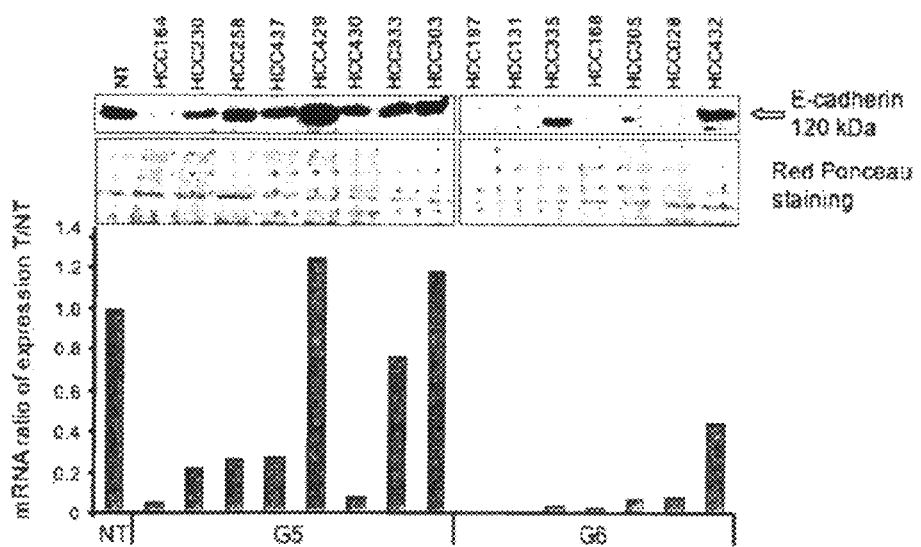

In G5 (CTNNB1 mutated, no distant nodules), an enrichment of under-expressed genes involved in stress and immune response such as IFI16, IL4R, IFI44, STAT1, IL10RA, CTSS and HLA-DPA1/B1 (P<0.002) was observed. HCC subgroups G5 and G6 contain 23 and 11 tumors CTNNB1 mutated in 70 and 100% of the cases, respectively. In a search for possible β-catenin targeted genes, a list of 280 genes significantly over-expressed in G5 and G6 was found. In addition to GPR49 and GLUL, two known β-catenin target genes in the liver (Cadoret, A. et al. Oncogene 21, 8293-301 (2002); Yamamoto, Y. et al. Hepatology 37, 528-33 (2003)), the over-expression of 7 putative β-catenin target genes was confirmed using QRT-PCR. These genes include: EPHB2, a tyrosine kinase receptor; MME, the enkephalinase CD10; MERTK, an oncogene tyrosine kinase; LAMA3, encoding the alpha-3 chain of the laminin 5; PAP/HIP, encoding a pancreatitis associated protein; SPARCL1 encoding hevin which is associated with extracellular matrix; and the transcription factor TBX3 (FIG. 4a). A significant higher level of expression of all these putative β-catenin targeted genes was observed in G6 when compared with G5, even after exclusion of the samples without CTNNB1 mutation. It was also shown that β-catenin was more over-expressed in G6 tumors, when compared with G5 tumors, with a loss of signal at the plasma membrane and a strong localization in cytoplasm and nucleus (FIG. 4b). Consistent with this observation, an over-expression of LEF1, a transcription factor that interacts with β-catenin to activate Wnt-responsive target genes, was found in G6. While both G5 and G6 subgroups were associated with chromosome 8p LOH, no other chromosome deletion specific of G6 was identified. However, an under-expression of CDH1 (encoding the E-cadherin) was found in G6 subgroup (in Affymetrix and QRT-PCR experiments, FIG. 4a) that may account for the local invasion of these HCC as shown by the quasi-constant presence of satellite nodules found around the principal tumor (FIG. 4c and Tables 1 and 2). The level of CDH1 mRNA down-regulation was showed to be highly related to the down-regulated expression of the E-cadherin protein in G6 consistent with the high level of promoter methylation of CDH1 in these tumors (data not shown).

2.3 Conclusion

Using a non-supervised, genome-wide approach, the inventors obtained a robust classification of HCC in 6 main subgroups reflecting the natural large diversity of these tumors (Bosch, F. X., et al. Gastroenterology 127, S5-S16 (2004); El-Serag, H. B. Gastroenterology 127, S27-34 (2004)). In addition, this classification could be reproduced using only 16 genes analyzed with QRT-PCR and, more importantly, was confirmed in an independent set of tumors.

This classification is in agreement with the previously published analyses of HCC (Lee, J. S. et al. Hepatology 40, 667-76 (2004); Breuhahn, K. et al. Cancer Res 64, 6058-64 (2004); Chen, X. et al. Mol Biol Cell 13, 1929-39 (2002)) that have described two main groups of tumors related to chromosome stability (corresponding to the meta-groups G1-G3 and G4-G6). However, the present analysis has extended and refined this classification.

Figure 1:
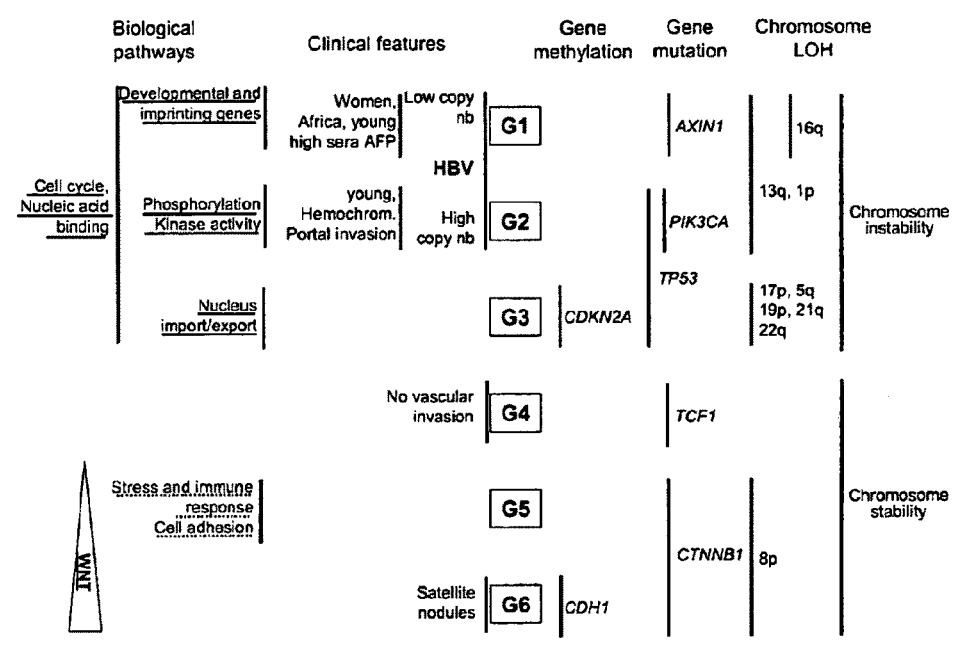

In short, the inventors believe that the elucidation of the multifaceted classification of HCC was only possible in this application, compared to the previous published classifications into two subgroups, because (1) the studied series of tumors surgically treated in France included the main different risk factors of HCC, i.e. HBV and HCV infections, alcohol abuse and hemochromatosis and (2) the large number of clinical, histopathological and genetic annotations available for the studied sample population. Indeed, the main clinical determinant of class membership is the HBV infection whereas the other main determinants are genetic and epigenetic alterations including chromosome instability, TP53 and CTNNB1 mutations, CDKN2A and CDH1 methylation and the parental imprinting (see FIG. 1).

Focusing on the natural history of HCC, it appears that HBV related tumors defining G1 and G2 subgroups are clearly molecularly distinct from the other etiologies. Tumors related to HCV infection and alcohol abuse are interspersed within the subgroups G3 to G6. The present transcriptomic classification has enabled the identification of new entities of tumors. Subgroup G1 includes HBV related tumors from younger patients (relative to the other HBV HCCs), frequently from Africa, with an equal sex ratio, a low number of viral DNA copies, frequent AXIN1 mutations, absence of TP53 mutation and an over-expression of genes normally parentally imprinted. These results suggest that HBV infection at the early age leads to a specific type of HCC demonstrating immature features with an abnormal parental gene imprinting possibly through the persistence of fetal hepatocytes or through the dedifferentiation of adult hepatocytes. Such diversity in tumors may be related to the high-risk populations found by epidemiological studies (Brechot, C. *Gastroenterology* 127, S56-61 (2004); Yu, M. C. & Yuan, J. M. *Gastroenterology* 127, S72-8 (2004)).

Subgroup G6 with a 100% incidence of CTNNB1 mutation, a high level of pathological Wnt pathway activation (higher than in G5) and inactivation of E-cadherin (Kozyraki, R. et al. *Gastroenterology* 110, 1137-49 (1996)) is consistent with the high invasive potential of these tumors as E-cadherin inactivation is known to participate in cell invasion process (Behrens, J., et al. *J Cell Biol* 108, 2435-47 (1989)).

Apart of these large subgroups of tumors, the present transcriptomic analysis has also suggested homogeneous subgroups of tumors related to rare genetic alterations like TCF1 or PIK3CA mutations (Bluteau, O. et al. *Nat Genet* 32, 312-5 (2002); Lee, J. W. et al. *Oncogene* 24, 1477-80 (2005)). New structural gene alterations characteristic of other small homogeneous subgroups of tumors remained to be identified and conversely, this can be a powerful tool to find new therapeutic targets.

Example 3

Prognosis of HCC Tumors 3.1 Material and Methods
Quantitative RT-PCR Analysis
Quantitative RT-PCR analysis was performed as described in the Material and Methods section of Example 2.
Construction of Prognosis Predictor
Based on the $2^{-\Delta Ct}$ values ($\Delta Ct=Ct_{TESTED}-Ct_{R18S}$) for 135 genes from the series of 42 samples analyzed with Affymetrix GeneChips, the top 16 genes (maximum logrank $P \leq 10^{-2}$) associated with prognostic status (Global Survival at 60 months) were identified using a univariate Cox model (package survival V2.15). Using the same 42 samples, the best combinations of 5 genes or less among these 16 genes (maximum logrank $P<10^{-5}$) was then selected using a multivariate Cox model from all possible combinations. A second series of 53 independent HCC was then used to validate those models (maximum logrank $P<10^{-3}$), retaining 42 of them. The robustness of each model was further assessed with the following resampling approach: we obtained 1,000 samplings by dividing 1,000 times, randomly, the whole series of 95 tumors in 2 groups of 47 and 48 samples each (equilibrating the number of death events between both groups); then, using each of the 42 lists of genes, for both groups of each sampling, multivariate Cox models were constructed and the logrank P value calculated from both models were stored. The combination of genes leading to the lowest median logrank P in both groups (among those 1,000 samplings) was kept and a predictor was then derived from this combination.

3.2 Results
Identification and Validation of Genes Predicting Prognosis
Although diagnostically useful, the 16-gene classification signature (see Example 2) did not suffice in predicting HCC prognosis as logrank tests yielded high p values of (P=0.2 and 0.1) testing either the two main groups of tumors (G1 to G3 vs G4 to G6) or the individual 6-subgroups, respectively. As a result, a specific predictor of prognosis was constructed as described in the Material and Methods section.

Globally, genes found to be useful for prognostic of global survival and/or survival without relapse were those listed in the above described Table 7.

More precisely, the top 16 genes associated with prognostic status of global survival were determined to be: NRCAM, PIR, RAMP3, SLC21A2, TAF9, TNA, HN1, PSMD1, MRPS7, CDC20, ENO1, HLF, STRA13, RAGD, NRAS, ARFGEF2.

After testing of all possible combinations of 5 genes or less among these 16 genes as described in Material and Methods, the 5 best models predicted global survival using a multivariate Cox analysis with a $P<10^{-8}$. Finally the most useful combination to predict the bad overcome is the association of 5 genes: a low level of RAMP3 combined with a high level of TAF9, NRCAM, PSMD1 and ARFGEF2.

The best global survival predictor follows the following formulas:

$$\text{Global survival score}(sample_i) = \sum_t \beta(gene_t) \cdot (2^{-\Delta Ct(sample_i, gene_t)} - \mu(gene_t)),$$

wherein the different $\beta(gene_t)$ and $\mu(gene_t)$ parameters are those listed in the following Table 11.

TABLE 11

Parameters to be used in the above formula for the best out of top 5 overall survival predictors

| Global survival | μ | β |
|---|---|---|
| gene 1 (TAF9) | 7.28 | 0.129 |
| gene 2 (NRCAM) | 1.59 | 0.252 |
| gene 3 (RAMP3) | 0.14 | −6.133 |
| gene 4 (PSMD1) | 4.66 | 0.024 |
| gene 5 (ARFGEF2) | 3.66 | −0.025 |

Results for the best predictor of global survival in term of ROC curve, Score curve and Survival curves are displayed in FIG. 5a, while statistics related to this best predictor of global survival are listed in the following Table 12.

TABLE 12

Statistics related to global survival predictor (for training and validation sets)

| | Global survival | |
|---|---|---|
| | Training set | Validation set |
| Area under curve | 0.88 | 0.67 |
| Specificity | 72.8% | 70% |
| Sensibility | 88.8% | 73.6% |
| Fisher exact test P | 4 $10^{-5}$ | 9 $10^{-5}$ |
| Success rate | 80.9% | 79.2% |

In the 53 HCC validation set, this combination of genes correctly predicted early relapse in 79% of the cases (70% for (+), 89% for (−)); and early deaths were correctly predicted in 81% of the cases (73% for (+); 92% for (−)). Among the clinical and morphological features, Edmondson grade and vascular invasion were significantly associated with a poor prognosis (logrank P<0.04 and 0.0002 respectively). A multivariate Cox model including these two variables plus the best global survival predictor was performed (see following Table 13). This model shows that our gene combination is an independent prognostic variable.

TABLE 13

Hazard Ratio (HR), logrank P-value (P) and 95% Confidence Interval (CI) from the multivariate Cox model obtained (for overall survival) using the following predictive variables: (i) binary attribution (above or below score threshold) for the best overall survival predictor, (ii) vascular invasion and (iii) Edmondson grade (grade I and II were merged, as only 7 cases were available for grade I).

|  | HR | P | 95% CI |
|---|---|---|---|
| Gene predictor | 7.8 | 0.00001 | 3.1-19.7 |
| Vascular invasion | 2.6 | 0.02 | 1.2-5.8 |
| Edmondson grade III | 0.5 | 0.09 | 0.2-1.1 |
| Edmondson grade IV | 2.8 | 0.14 | 0.7-10.6 |

The same strategy was applied to find combinations of genes predicting the disease-free survival. Interestingly, among the top 16 genes (TAF9, NRCAM, ENO1, RAB1A, ARFGEF2, G0S2, PSMD1, MRPS7, RAGD, HN1, PIR, SMAD3, DNAJA3, HELO1, RAMP3, RHOQ), ten were previously identified as the best predictors of the overall survival using univariate Cox model. Finally, all 3 genes included in the best predictor of the disease-free survival were also included in the best predictor of the overall survival.

The best survival without relapse (or disease-free) predictor follows the following formulas:

$$\text{Disease-free score}(sample_i) = \sum_t \beta(gene_t) \cdot (2^{-\Delta Ct(sample_i, gene_t)} - \mu(gene_t)),$$

wherein the different $\beta(gene_t)$ and $\mu(gene_t)$ parameters are those listed in the following Table 14.

TABLE 14

Parameters to be used in the above formula) for the best out of top 5 disease free survival predictors.

| Disease Free survival | μ | β |
|---|---|---|
| gene 1 (TAF9) | 7.28 | 0.127 |
| gene 2 (NRCAM) | 1.59 | 0.196 |
| gene 3 (RAMP3) | 0.14 | −3.886 |

Figure 5B:
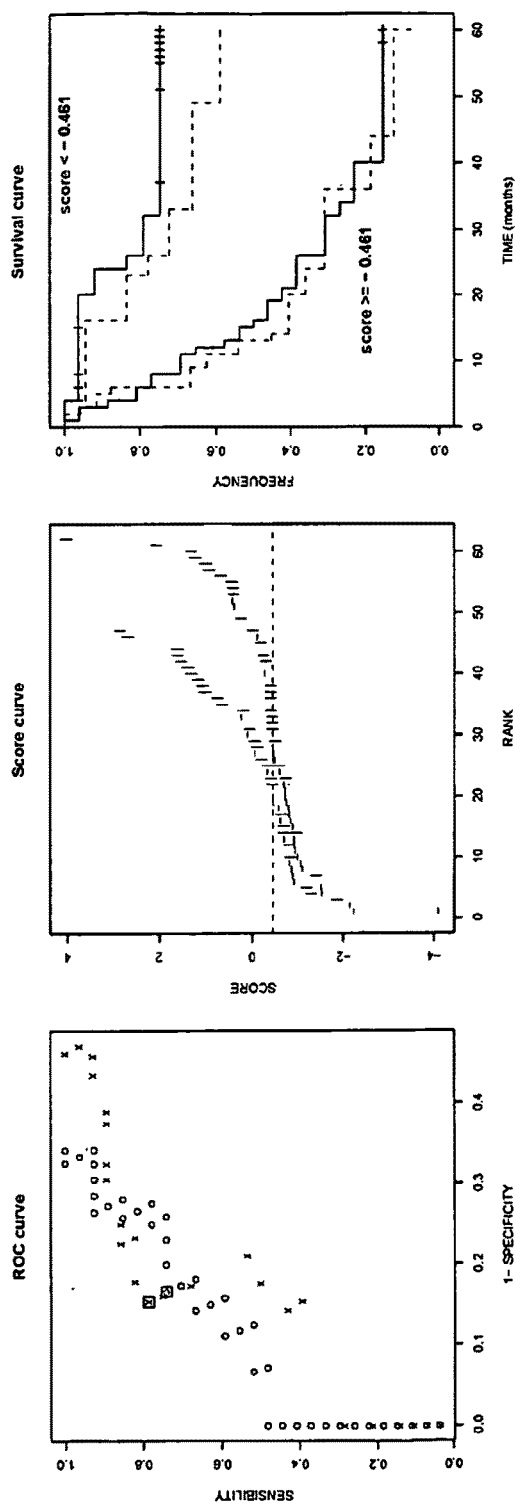

Results for the best predictor of global survival in term of ROC curve, Score curve and Survival curves are displayed in FIG. 5b, while statistics related to this best predictor of global survival are listed in the following Table 15.

TABLE 15

Statistics related to the best disease free survival predictor.

| | Disease Free Survival | |
|---|---|---|
| | Training set | Validation set |
| Area under curve | 0.86 | 0.84 |
| Specificity | 83.4% | 84.7% |
| Sensibility | 74% | 78.5% |
| Fisher exact test P | $4\ 10^{-3}$ | $6\ 10^{-6}$ |
| Success rate | 73.8% | 81.1% |
| Logrank P | $3\ 10^{-4}$ | $7\ 10^{-6}$ |

3.3 Conclusion

Elucidation of the transcriptomic classification is of particular interest for clinical applications. In particular, it appears that HCC belonging to groups G1 to G3 were slightly related to early relapse and early death compared to HCC from G4 to G6, showing that classification and prognosis are somehow related.

However, the inventors found that using a small specific subset of about 5 genes was superior than using the global classification 16-gene signature in predicting the prognosis of patients treated by complete surgical resection. In contrast to previous published transcriptomic analyses, the performance of the determined survival predictor was verified in a second set of independent tumors including all etiological risk factors and such validations were performed using QRT-PCR in place of hybridization data (Lee, J. S. et al. Hepatology 40, 667-76 (2004); Ye, Q. H. et al. Nat Med 9, 416-23 (2003); Iizuka, N. et al. Lancet 361, 923-9 (2003); Kurokawa, Y. et al. J Hepatol 41, 284-91 (2004)).

The genes identified in the present applications as useful to predict survival had never been previously found associated to patient prognosis and they may be implicated in general cellular processes such as proteasome degradation of proteins (PSMD1, see Yokota, K. et al. Mol Biol Cell 7, 853-70 (1996)), the initiation of RNA transcription (TAF9, see Michel, B., Komarnitsky, P. & Buratowski, S. Mol Cell 2, 663-73 (1998)) and cellular proliferation (NRCAM, see Sehgal, A., et al. Anticancer Res 19, 4947-53 (1999); and ARF-GEF2, see Sheen, V. L. et al. Nat Genet 36, 69-76 (2004)).

Interestingly, the best combinations of genes predicting global survival as well as disease-free survival (i.e. survival without relapse) were very similar in this study demonstrating that the determined predictors accurately reflects tumor progression irrespective of non-tumor related hepatic disease.

It would be also very interesting to evaluate these predictors in patients treated with liver transplantation or radiofrequency in order to estimate the potential usefulness of these markers in the therapeutic choice.

In conclusion, the present global transcriptomic analysis has been carried out and validated using a large series of highly annotated tumors. This analysis has established a robust classification reflecting the natural diversity of human HCCs, the structural gene alterations and epigenetic de-regulations accumulated during tumor progression. The high diversity of HCC tumor has clinical implications and the present classification has yielded prognostic tools not only for surgically treated patients but also to further identify patients that will benefit of targeted therapies.

BIBLIOGRAPHY

1. Bosch. F. X., et al. Semin Liver Dis 19, 271-85 (1999)
2. Taylor-Robinson, S. D. et al. Bmj 319, 640 (1999);
3. Deuffic, S. et al. Lancet 351, 214-5 (1998).
4. El-Serag, H. B. & Mason, A. C. N Engl J Med 340, 745-50 (1999)
5. Edmondson, H. A. & Peters, R. L. Semin Roentgenol 18, 75-83 (1983);
6. Thorgeirsson, S. S. & Grisham, J. W. Nat Genet 31, 339-46 (2002)).
7. Aoki, H., et al. Proc Natl Acad Sci USA 93, 7300-4 (1996)
8. Brechot, C. Gastroenterology 127, S56-61 (2004)
9. Bressac, B. et al. Proc Natl Acad Sci USA 87, 1973-7 (1990)
10. Weihrauch, M. et al. Br J Cancer 84, 982-9 (2001)
11. Bluteau, O. et al. Nat Genet 32, 312-5 (2002)
12. Boige, V. et al. Cancer Res 57, 1986-90 (1997);

13. Wong, N. et al. Clin Cancer Res 6, 4000-9 (2000);
14. Guan, X. Y. et al. Genes Chromosomes Cancer 29, 110-6 (2000)
15. Okabe et al. Cancer Res. 2001 Mar. 1; 61(5):2129-37;
16. Iizuka et al. Cancer Res. 2002 Jul. 15; 62(14):3939-44
17. Chung et al. Mol Cells. 2002 Dec. 31; 14(3):382-7;
18. Chen et al. Mol Biol Cell. 2002 June; 13(6):1929-39;
19. WO 2004/090163
20. Lee et al. Hepatology. 2004 September; 40(3):667-76
21. Legoix, P. et al. Oncogene 18, 4044-6 (1999);
22. Laurent-Puig, P. et al. Gastroenterology 120, 1763-73 (2001)
23. Qin et al. J Cancer Res Clin Oncol. 2004 September; 130(9):497-513;
24. Ye et al. Nat Med. 2003 April; 9(4):416-23
25. Kurokawa et al. J Hepatol. 2004 August; 41(2):284-91
26. Iizuka et al. Lancet. 2003 Mar. 15; 361(9361):923-9;
27. WO 2005/017150
28. Lee, S. et al. Am J Pathol 163, 1371-8 (2003);
29. Zochbauer-Muller, S. et al. Cancer Res 61, 249-55 (2001)
30. Livak, K. J. & Schmittgen, T. D. Methods 25, 402-8 (2001)
31. Cadoret, A. et al. Oncogene 21, 8293-301 (2002);
32. Yamamoto, Y. et al. Hepatology 37, 528-33 (2003)
33. Bosch, F. X., et al. Gastroenterology 127, S5-S16 (2004);
34. El-Serag, H. B. Gastroenterology 127, S27-34 (2004)
35. Breuhahn, K. et al. Cancer Res 64, 6058-64 (2004);
36. Yu, M. C. & Yuan, J. M. Gastroenterology 127, S72-8 (2004)
37. Kozyraki, R. et al. Gastroenterology 110, 1137-49 (1996)
38. Behrens, J., et al. J Cell Biol 108, 2435-47 (1989)
39. Lee, J. W. et al. Oncogene 24, 1477-80 (2005)
40. Yokota, K. et al. Mol Biol Cell 7, 853-70 (1996)
41. Michel, B., Komarnitsky, P. & Buratowski, S. Mol Cell 2, 663-73 (1998)
42. Sehgal, A., et al. Anticancer Res 19, 4947-53 (1999);
43. Sheen, V. L. et al. Nat Genet 36, 69-76 (2004)).

The invention claimed is:

1. A method for the classification of a hepatocellular carcinoma (HCC) tumor between six subgroups from a liver HCC sample of a human subject suffering from HCC, comprising:
   a) measuring, in vitro, the nucleic acid expression level of a group of selected genes in said liver HCC sample, wherein the group of selected genes comprises a combination of at least eight genes selected from the group consisting of: RAB1A, REG3A, NRAS, RAMP3, MERTK, PIR, EPHA1, LAMA3, GOS2, HN1, PAK2, AFP, CYP2C9, CDH2, HAMP, SAE1, ADH6, DCN, FLJ10159, ALDH1L1, IGF1, LECT2, SLC38A1, SPARCL1, CTNNA2, GLUL, LEF1, MATN2, MME, PFN2, SPINT2, TBX3, and FGFR2;
   b) determining from said measurement an expression profile of said selected genes;
   c) calculating from said expression profile a distance between said expression profile and a center point in n-dimensional space of each of six subgroups, G1, G2, G3, G4, G5, and G6, each subgroup being defined by the presence (+) or absence (−) of their clinical and genetic features described in the following Table:

|  | G1 | G2 | G3 | G4 | G5 | G6 |
|---|---|---|---|---|---|---|
| Chromosome instability | + | + | + | − | − | − |
| Early relapse and death | + | + | + | − | − | − |
| TP53 mutation | − | + | + | − | − | − |
| HBV infection | + | + | − | − | − | − |
| Low copy number | + | − | − | − | − | − |
| High copy number | − | + | − | − | − | − |
| CTNNB1 mutation | − | − | − | − | + | + |
| Satellite nodules | − | − | − | − | − | + | and where the number of dimensions n is the number of genes measured and coordinates of the n-dimensional space correspond to expression levels; and d) classifying said HCC tumor in the subgroup for which the value of the distance between the expression profile of said liver HCC sample and the center point of the subgroup is minimal.

2. The method of claim 1, wherein the group of selected genes comprises a combination of the following 16 genes consisting of: RAB1A, REG3A, NRAS, RAMP3, MERTK, PIR, EPHA1, LAMA3, GOS2, HN1, PAK2, AFP, CYP2C9, CDH2, HAMP, and SAE1.

3. The method of claim 1, wherein the expression profile is determined employing quantitative PCR.

4. The method of claim 1, wherein the group of selected genes is a combination of the following 16 genes consisting of: RAB1A, REG3A, NRAS, RAMP3, MERTK, PIR, EPHA1, LAMA3, GOS2, HN1, PAK2, AFP, CYP2C9, CDH2, HAMP, and SAE1, and wherein the distance between the expression profile of the liver HCC sample and each subgroup $G_k$, is calculated using the following formula:

$$\text{Distance (sample, } G_k) = \sum_{t=1 \ldots 16} \frac{(\Delta Ct(\text{sample, gene}_t) - \mu(G_k, \text{gene}_t))^2}{\sigma(\text{gene}_t)},$$

wherein $1 \leq k \leq 6$, and for each $\text{gene}_t$ and subgroup $G_k$, the $\mu(G_k, \text{gene}_t)$ and $\sigma(\text{gene}_t)$ values are in an interval of 10% around those displayed in the following Table:

| μ | $G_1$ | $G_2$ | $G_3$ | $G_4$ | $G_5$ | $G_6$ | σ |
|---|---|---|---|---|---|---|---|
| gene 1 (RAB1A) | −16.39 | −16.04 | −16.29 | −17.15 | −17.33 | −16.95 | 0.23 |
| gene 2 (PAP) | −28.75 | −27.02 | −23.48 | −27.87 | −19.23 | −11.33 | 16.63 |
| gene 3 (NRAS) | −16.92 | −17.41 | −16.25 | −17.31 | −16.96 | −17.26 | 0.27 |
| gene 4 (RAMP3) | −23.54 | −23.12 | −25.34 | −22.36 | −23.09 | −23.06 | 1.23 |

-continued

| μ | G$_1$ | G$_2$ | G$_3$ | G$_4$ | G$_5$ | G$_6$ | σ |
|---|---|---|---|---|---|---|---|
| gene 5 (MERTK) | −18.72 | −18.43 | −21.24 | −18.29 | −17.03 | −16.16 | 7.23 |
| gene 6 (PIR) | −18.44 | −19.81 | −16.73 | −18.28 | −17.09 | −17.25 | 0.48 |
| gene 7 (EPHA1) | −16.68 | −16.51 | −19.89 | −17.04 | −18.70 | −21.98 | 1.57 |
| gene 8 (LAMA3) | −20.58 | −20.44 | −20.19 | −21.99 | −18.77 | −16.85 | 2.55 |
| gene 9 (G0S2) | −14.82 | −17.45 | −18.18 | −14.78 | −17.99 | −16.06 | 3.88 |
| gene 10 (HN1) | −16.92 | −17.16 | −15.91 | −17.88 | −17.72 | −17.93 | 0.54 |
| gene 11 (PAK2) | −17.86 | −16.56 | −16.99 | −18.14 | −17.92 | −17.97 | 0.58 |
| gene 12 (AFP) | −16.68 | −12.36 | −26.80 | −27.28 | −25.97 | −23.47 | 14.80 |
| gene 13 (CYP2C9) | −18.27 | −16.99 | −16.26 | −16.23 | −13.27 | −14.44 | 5.47 |
| gene 14 (CDH2) | −15.20 | −14.76 | −18.91 | −15.60 | −15.48 | −17.32 | 10.59 |
| gene 15 (HAMP) | −19.53 | −20.19 | −21.32 | −18.51 | −25.06 | −26.10 | 13.08 |
| gene 16 (SAE1). | −17.37 | −17.10 | −16.79 | −18.22 | −17.72 | −18.16 | 0.31 |

5. A method for the classification of a hepatocellular carcinoma (HCC) tumor between six subgroups from a liver HCC sample of a human subject suffering from HCC, comprising:
   a) determining an expression profile of said liver HCC sample by measuring, in vitro, the nucleic acid expression level of a group of selected genes in said liver HCC sample, wherein the group of selected genes comprises a combination of at least eight genes selected from the group consisting of: ALDH1L1, CD24, CD74, CFHR3, CYP4F12, DNAJA3, DSCR1, EPHA1, EPHB4, FAAH, FGFR2, FLJ10159, GLT8D1, HAL, MATN2, MRPS7, PAK2, PLXNB1, RAB1A, RHOQ, SLC27A5, SLPI, SMARCE1, and STRA13;
   b) calculating a distance between said expression profile and a center point in n-dimensional space of each of six subgroups, G1, G2, G3, G4, G5, and G6, where n is the number of genes measured and coordinates of the n-dimensional space correspond to expression levels; and
   c) classifying said HCC tumor in the subgroup for which the value of the distance between the expression profile of liver HCC sample and the center point of the subgroup is minimal,
   wherein the six subgroups G1, G2, G3, G4, G5, and G6 are defined by the presence (+) or absence (−) of their clinical and genetic features described in the following Table:

| | G1 | G2 | G3 | G4 | G5 | G6 |
|---|---|---|---|---|---|---|
| Chromosome instability | + | + | + | − | − | − |
| Early relapse and death | + | + | + | − | − | − |
| TP53 mutation | − | + | + | − | − | − |
| HBV infection | + | + | − | − | − | − |
| Low copy number | + | − | − | − | − | − |
| High copy number | − | + | − | − | − | − |
| CTNNB1 mutation | − | − | − | − | + | + |
| Satellite nodules | − | − | − | − | − | +. |

6. The method of claim 5, wherein the group of selected genes comprises a combination of the following 24 genes consisting of: ALDH1L1, CD24, CD74, CFHR3, CYP4F12, DNAJA3, DSCR1, EPHA1, EPHB4, FAAH, FGFR2, FLJ10159, GLT8D1, HAL, MATN2, MRPS7, PAK2, PLXNB1, RAB1A, RHOQ, SLC27A5, SLPI, SMARCE1, and STRA13.

7. The method of claim 6, wherein the expression profile is determined employing a nucleic acid microarray.

8. The method of claim 7, wherein the group of selected genes is a combination of the following 24 genes consisting of: ALDH1L1, CD24, CD74, CFHR3, CYP4F12, DNAJA3, DSCR1, EPHA1, EPHB4, FAAH, FGFR2, FLJ10159, GLT8D1, HAL, MATN2, MRPS7, PAK2, PLXNB1, RAB1A, RHOQ, SLC27A5, SLPI, SMARCE1, and STRA13, and wherein the value of the mathematical distance between the expression profile of the liver HCC sample and each subgroup $G_k$ is calculated using the following formula:

$$\text{Distance}(sample, G_k) = \left( \frac{\sum_{t=1\ldots 24}(c(gene_t, G_k))^2}{2} + 1.791759 \right) - \left( \sum_{t=1\ldots 24} \frac{(y(sample, gene_t) - \mu(gene_t))}{\sigma(gene_t)} \times c(gene_t, G_k) \right) \quad (V)$$

wherein for each $gene_t$ and subgroup $G_k$, $c(gene_t, G_k)$, $\mu(gene_t)$ and $\sigma(gene_t)$ values are in an interval of 10% around those displayed in the following Table:

| Gene N° | Gene symbol | $G_1$ | $G_2$ | $G_3$ | $G_4$ | $G_5$ | $G_6$ | μ | σ |
|---|---|---|---|---|---|---|---|---|---|
| 1 | MATN2 | 0.70615962 | 0.194820133 | 0 | 0.251226887 | −0.43679693 | −0.95672006 | 6.86694444 | 1.3591753 |
| 2 | EPHB4 | 0.772905372 | 0 | −0.23845281 | 0 | 0 | −0.11554095 | 8.12722222 | 0.90851011 |
| 3 | SLPI | 0.348202773 | 1.150217317 | −0.30674955 | 0.772922695 | −0.92749405 | −1.03709919 | 9.19555556 | 1.58143433 |
| 4 | FAAH | 0 | −0.05721942 | −0.14546431 | 0.461062372 | 0 | 0 | 7.35527778 | 0.90656803 |
| 5 | ALDH1L1 | −0.90005519 | −0.88021827 | 0 | 0.001883282 | 0.766706969 | 0.727033118 | 9.55166667 | 1.51233112 |
| 6 | DNAJA3 | −0.38971634 | 0 | 0 | 0 | 0.115122957 | 0 | 9.20444444 | 0.79106866 |
| 7 | EPHA1 | 0.084999966 | 1.076607341 | −0.39390753 | 0.336075517 | −0.15411627 | −0.94965903 | 8.34 | 1.18158325 |
| 8 | CYP4F12 | 0 | 0 | −0.50724032 | 0 | 0.411786437 | 0 | 8.61416667 | 0.89048235 |
| 9 | CFHR4 /// CFHR3 | −0.3047186 | 0 | −0.85911235 | 0.594911312 | 0.240167858 | 0 | 9.63111111 | 1.9450676 |
| 10 | FGFR2 | 1.107271104 | 1.414413219 | 0 | −0.33319985 | −0.93870859 | −0.78623447 | 6.45694444 | 1.51938352 |
| 11 | CD24 | 0.877735471 | 0.272141138 | 0.391097168 | −0.19493988 | −0.09580985 | −1.25022405 | 6.88527778 | 1.84942286 |
| 12 | RAB1A | 0 | 0.181176347 | 0.101889323 | 0 | −0.13052075 | 0 | 10.9441667 | 0.75674426 |
| 13 | PAK2 | 0.333384856 | 0 | 0.506491717 | −0.14545539 | −0.07557739 | −0.39796907 | 7.58722222 | 1.04944811 |
| 14 | STRA13 | −0.61853503 | −0.18082898 | 0.428679271 | −0.14603227 | 0.113677426 | 0.403039586 | 9.56055556 | 0.91004758 |
| 15 | CD74 | −0.20143371 | 0 | 0 | 0 | −0.40543025 | 0.741093354 | 10.9897222 | 1.28270148 |
| 16 | SMARCE1 | 0.126430939 | 0 | 0.308479215 | −0.17753221 | 0 | −0.25610041 | 8.43638889 | 0.86973267 |
| 17 | RHOQ | 0 | 0.321593401 | 0.234570894 | 0 | −0.196463 | −0.09749623 | 8.02888889 | 0.97675881 |
| 18 | DSCR1 | −0.04133466 | −0.10070514 | −0.07191945 | 0.033538532 | 0 | 0.436538207 | 7.40194444 | 0.92638619 |
| 19 | PLXNB1 | 0.550893643 | 0.055723559 | −0.24782026 | −0.15487024 | 0 | −0.08389023 | 8.10722222 | 0.98619313 |
| 20 | HAL | 0.428036608 | 1.655082264 | −0.24462171 | 0.139158147 | −0.85676893 | −1.12088638 | 7.73055556 | 1.21158219 |
| 21 | MRPS7 | −0.24232641 | 0 | 0.552001257 | 0 | 0 | 0 | 8.77777778 | 0.88623422 |
| 22 | GLT8D1 | −0.08380816 | −0.21624193 | −0.11283474 | 0 | 0.458734818 | 0.34625682 | 9.20027778 | 0.91869819 |
| 23 | FLJ10159 | 1.275819214 | 0.257162026 | 0 | −0.03229518 | −0.27448613 | −0.99690117 | 7.33638889 | 1.60341806 |
| 24 | SLC27A5 | −0.93094948 | −0.2491716 | −0.50142942 | 0.607483755 | 0.535897078 | 0.538169671 | 9.89388889 | 1.46675337. |

9. The method of claim 1, wherein the liver HCC sample is a liver HCC biopsy or a HCC tumor surgical resection.

10. The method of claim 5, wherein the liver HCC sample is a liver HCC biopsy or a HCC tumor surgical resection.

11. The method as defined in any one of claims 1-4, further comprising calculating a prognosis based upon said classification.

12. The method as defined in any one of claims 1-4, further comprising calculating a prognosis based upon said classification and administering treatment to the subject based upon the prognosis.

13. The method as defined in any one of claims 1-4, further comprising determining a survival and/or survival without relapse prognosis based upon said classification and administering an adjuvant therapy if the prognosis predicts low survival or high possibility of relapse.

14. The method as defined in any one of claims 1-4, further comprising administering to said subject a therapeutic treatment targeted to the HCC subgroup to which the HCC tumor sample belongs.

15. The method as defined in any one of claims 5-7, further comprising calculating a prognosis based upon said classification.

16. The method as defined in any one of claims 5-7, further comprising calculating a prognosis based upon said classification and administering treatment to the subject based upon the prognosis.

17. The method as defined in any one of claims 5-7, further comprising determining a survival and/or survival without relapse prognosis based upon said classification and administering an adjuvant therapy if the prognosis predicts low survival or high possibility of relapse.

18. The method as defined in any one of claims 5-7, further comprising administering to said subject a therapeutic treatment targeted to the HCC subgroup to which the HCC tumor sample belongs.

* * * * *